(12) United States Patent
Fontana et al.

(10) Patent No.: US 9,642,898 B2
(45) Date of Patent: May 9, 2017

(54) USE OF SERINE PROTEASE INHIBITORS IN THE TREATMENT OF NEUTROPENIA

(71) Applicants: Med Discovery S.A., Plan-les-Ouates (CH); University of Zurich, Zurich (CH)

(72) Inventors: Adriano Fontana, Zurich (CH); Mike Recher, Zurich (CH); Christoph Kundig, Lausanne (CH)

(73) Assignees: MED DISCOVERY S.A., Cointrin/Geneva (CH); UNIVERSITY OF ZURICH, Zurich (CH)

( * ) Notice: Subject to any disclaimer, the term of this patent is extended or adjusted under 35 U.S.C. 154(b) by 0 days.

(21) Appl. No.: 14/550,063

(22) Filed: Nov. 21, 2014

(65) Prior Publication Data
US 2015/0165004 A1 Jun. 18, 2015

Related U.S. Application Data

(62) Division of application No. 13/256,096, filed as application No. PCT/IB2010/051038 on Mar. 10, 2010, now abandoned.

(60) Provisional application No. 61/202,535, filed on Mar. 10, 2009.

(51) Int. Cl.
| | | |
|---|---|---|
| A61K 38/57 | (2006.01) | |
| A61K 35/15 | (2015.01) | |
| A61K 35/28 | (2015.01) | |
| A61K 38/17 | (2006.01) | |

(52) U.S. Cl.
CPC ............. *A61K 38/57* (2013.01); *A61K 35/15* (2013.01); *A61K 35/28* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 2003/0054445 A1 | 3/2003 | Chen et al. | |
| 2005/0176002 A1* | 8/2005 | Diamandis | C12Q 1/6886 435/6.14 |
| 2005/0260140 A1 | 11/2005 | White et al. | |
| 2006/0147973 A1 | 7/2006 | Chen et al. | |
| 2006/0269536 A1* | 11/2006 | Deperthes | C07K 14/8121 424/94.2 |
| 2014/0341881 A1* | 11/2014 | Deperthes | A61K 8/64 424/94.64 |

FOREIGN PATENT DOCUMENTS

| | | |
|---|---|---|
| WO | WO-2004/087912 A1 | 10/2004 |
| WO | WO-2006/090282 A2 | 8/2006 |
| WO | WO-2009035541 A1 | 3/2009 |

OTHER PUBLICATIONS

Aprikyan A A et al: "Neutrophil elastase-specific small molecule inhibitor restores inefficient production of myeloid cells observed in severe congenital neutropenia", Experimental Hematology (New York) vol. 35, No. 9, Suppl. 2, Sep. 2007, (p. 216), pp. 113-114.
Aprikyan Andrew A et al: "Small molecule inhibitor of neutrophil elastase restores impaired production of human myeloid cells observed in severe congenital neutropenia", Blood, vol. 110, No. 11, Part 1, Nov. 2007, Abstract 664, 1 page.
Aprikyan Andrew A et al: "Small molecule inhibitor of neutrophil elastase reverses the block of myeloid differentiation and restores impaired cell production observed in severe congenital neutropenia", Experimental Hematology, vol. 36, No. 7, Suppl. 1, Jul. 2008, (p. 139), pp. S80-S81.

\* cited by examiner

*Primary Examiner* — Chris R Tate
*Assistant Examiner* — Aaron J Kosar
(74) *Attorney, Agent, or Firm* — Oliff PLC

(57) ABSTRACT

The invention relates to therapeutic compounds which are inhibitors of serine proteases, to pharmaceutical compositions thereof and to their use in the treatment of the human or animal body. More specifically, the present invention relates to a method for the treatment of neutropenia comprising the administration to a subject in need thereof of a therapeutically effective amount of a serine protease inhibitor. The invention also comprises prevention of apoptosis of myeloid cells (1) during and after transfection of bone marrow cells performed for gene therapy, (2) during blood stem cell mobilization performed for reconstitution of hematopoiesis and (3) during infusion of cells of the myeloid lineage for reconstitution of hematopoiesis for gene therapy or for treatment of neutropenia by infusion of neutrophils.

12 Claims, 7 Drawing Sheets

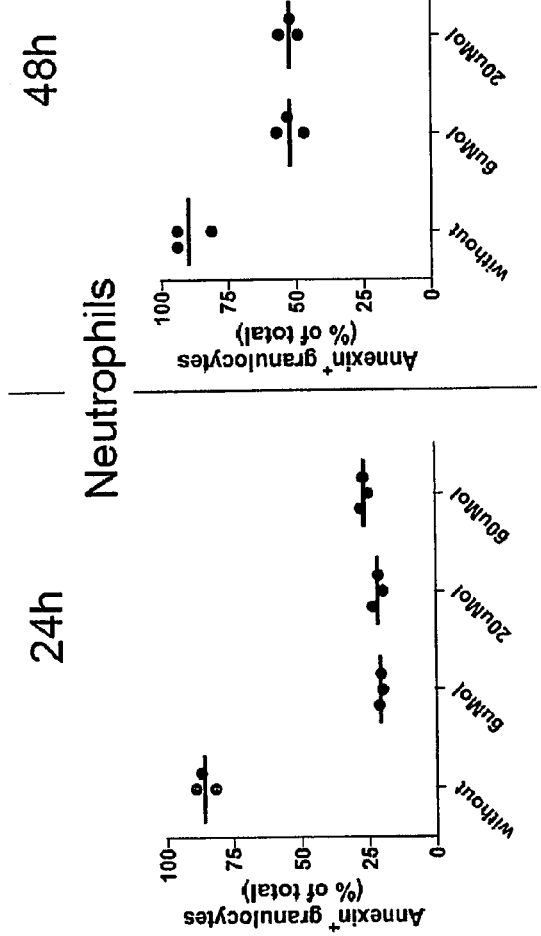
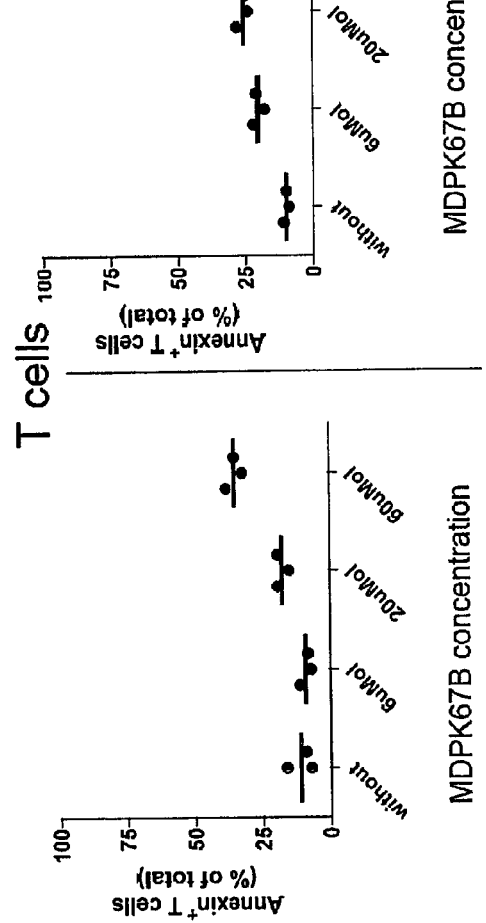

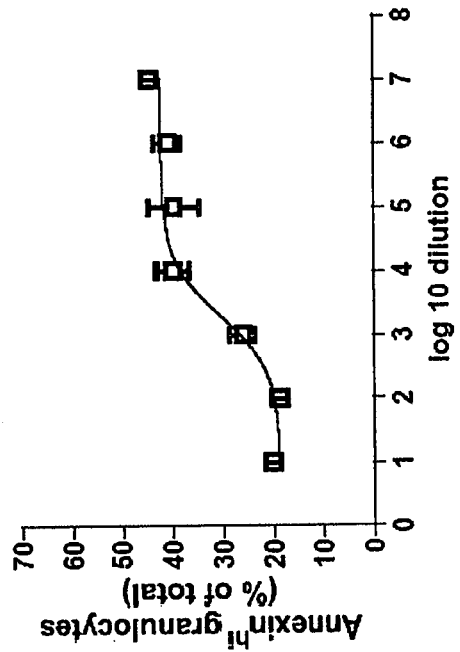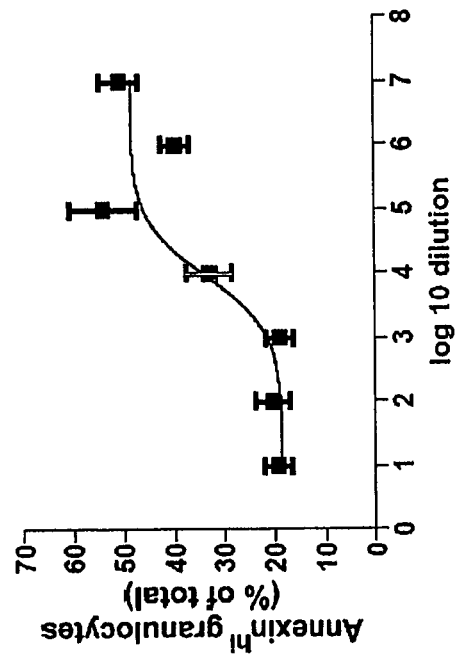
Fig. 2A
Fig. 2B

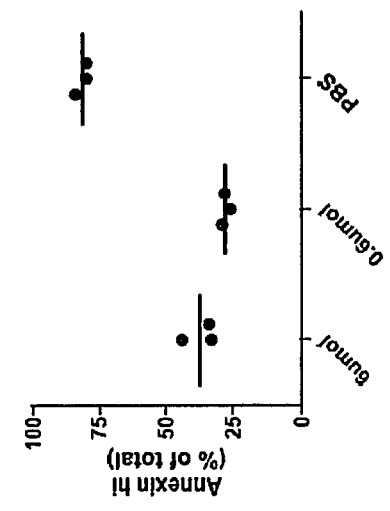
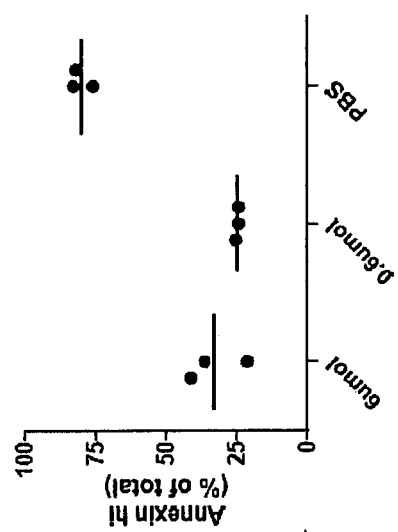
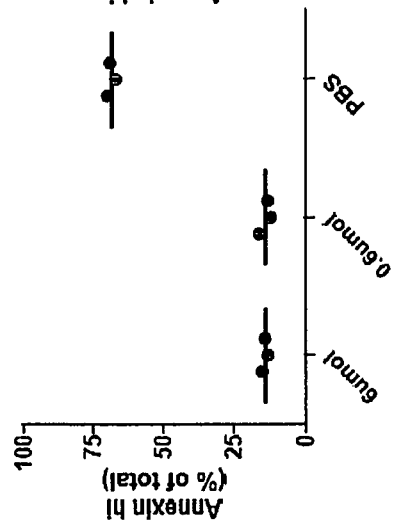

SEQUENCE LISTING

<160> NUMBER OF SEQ ID NOS: 74

<210> SEQ ID NO 1
<211> LENGTH: 1239
<212> TYPE: DNA
<213> ORGANISM: Artificial
<220> FEATURE:
<223> OTHER INFORMATION: synthetic sequence

<400> SEQUENCE: 1

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct ctccccact gagcatctcc accgccttgg ccttcctgtc tctgggggcc     240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggggaaa   540
atcacagatc tgatcaagga ccttgactcg cagacaatga tggtcctggt gaattacatc     600
ttctttaaag ccaaatggga gatgcccttt gaccccaag atactcatca gtcaaggttc      660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa agttttccat ctcgagggac tataacctga cgacatact tctccagctg      960
ggcattgagg aagcccttca cagcaaggct gacctgtcag gatcacagg ggccaggaac     1020
ctagcagtct cccaggtggt ccataaggct gtgcttgatg tatttgagga gggcacagaa    1080
gcatctgctg ccaccgcggt caaaatcacc ctccgttctc gagcagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 2
<211> LENGTH: 412
<212> TYPE: PRT
<213> ORGANISM: Artificial

<220> FEATURE:
<223> OTHER INFORMATION: synthetic sequence

<400> SEQUENCE: 2

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
            85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
            165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
            245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
            325                 330                 335

Gly Ala Arg Asn Leu Ala Val Ser Gln Val Val His Lys Ala Val Leu
        340                 345                 350

Asp Val Phe Glu Glu Gly Thr Glu Ala Ser Ala Ala Thr Ala Val Lys
    355                 360                 365

Ile Thr Leu Arg Ser Arg Ala Val Glu Thr Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
            405                 410

<210> SEQ ID NO 3
<211> LENGTH: 1239
<212> TYPE: DNA
<213> ORGANISM: Artificial
<220> FEATURE:
<223> OTHER INFORMATION: synthetic sequence

<400> SEQUENCE: 3

```
atgagaggat cccatcacca tcaccatcac tctagacacc ctaacagccc acttgacgag    60
gagaatctga cccaggagaa ccaagaccga gggacacacg tggacctcgg attagcctcc   120
gccaacgtgg acttcgcttt cagcctgtac aagcagttag tcctgaaggc ccctgataag   180
aatgtcatct tctccccact gagcatctcc accgccttgg ccttcctgtc tctgggggcc   240
cataatacca ccctgacaga gattctcaaa ggcctcaagt tcaacctcac ggagacttct   300
gaggcagaaa ttcaccagag cttccagcac ctcctgcgca ccctcaatca gtccagcgat   360
gagctgcagc tgagtatggg aaatgccatg tttgtcaaag agcaactcag tctgctggac   420
aggttcacgg aggatgccaa gaggctgtat ggctccgagg cctttgccac tgactttcag   480
gactcagctg cagctaagaa gctcatcaac gactacgtga agaatggaac taggggaaa    540
atcacagatc tgatcaagga ccttgactcg cagacaatga tggtcctggt gaattacatc   600
ttctttaaag ccaaatggga gatgccctt gaccccaag atactcatca gtcaaggttc    660
tacttgagca agaaaaagtg ggtaatggtg cccatgatga gtttgcatca cctgactata   720
ccttacttcc gggacgagga gctgtcctgc accgtggtgg agctgaagta cacaggcaat   780
gccagcgcac tcttcatcct ccctgatcaa gacaagatgg aggaagtgga agccatgctg   840
ctcccagaga ccctgaagcg gtggagagac tctctggagt tcagagagat aggtgagctc   900
tacctgccaa agttttccat ctcgaggggac tataacctga cgacatact ctctccagctg    960
ggcattgagg aagccttcac cagcaaggct gacctgtcag ggatcacagg ggccaggaac  1020
ctagcagtct cccaggtggt ccataaggct gtgcttgatg tatttgagga gggcacagaa  1080
gcatctgctg ccaccgcggt caaaatcacc aggaggtcta tcgatgtgga gacgcgtacc  1140
attgtgcgtt tcaacaggcc cttcctgatg atcattgtcc ctacagacac ccagaacatc  1200
ttcttcatga gcaaagtcac caatcccaag caagcctaa                         1239
```

<210> SEQ ID NO 4
<211> LENGTH: 412
<212> TYPE: PRT
<213> ORGANISM: Artificial
<220> FEATURE:
<223> OTHER INFORMATION: synthetic sequence

<400> SEQUENCE: 4

Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala

His Asn Thr Thr Leu Thr Glu Ile Leu Lys Gly Leu Lys Phe Asn Leu
 65                  70                  75                  80

Thr Glu Thr Ser Glu Ala Glu Ile His Gln Ser Phe Gln His Leu Leu
             85                  90                  95

Arg Thr Leu Asn Gln Ser Ser Asp Glu Leu Gln Leu Ser Met Gly Asn
            100                 105                 110

Ala Met Phe Val Lys Glu Gln Leu Ser Leu Leu Asp Arg Phe Thr Glu
        115                 120                 125

Asp Ala Lys Arg Leu Tyr Gly Ser Glu Ala Phe Ala Thr Asp Phe Gln
130                 135                 140

Asp Ser Ala Ala Ala Lys Lys Leu Ile Asn Asp Tyr Val Lys Asn Gly
145                 150                 155                 160

Thr Arg Gly Lys Ile Thr Asp Leu Ile Lys Asp Leu Asp Ser Gln Thr
                165                 170                 175

Met Met Val Leu Val Asn Tyr Ile Phe Phe Lys Ala Lys Trp Glu Met
            180                 185                 190

Pro Phe Asp Pro Gln Asp Thr His Gln Ser Arg Phe Tyr Leu Ser Lys
        195                 200                 205

Lys Lys Trp Val Met Val Pro Met Met Ser Leu His His Leu Thr Ile
    210                 215                 220

Pro Tyr Phe Arg Asp Glu Glu Leu Ser Cys Thr Val Val Glu Leu Lys
225                 230                 235                 240

Tyr Thr Gly Asn Ala Ser Ala Leu Phe Ile Leu Pro Asp Gln Asp Lys
                245                 250                 255

Met Glu Glu Val Glu Ala Met Leu Leu Pro Glu Thr Leu Lys Arg Trp
            260                 265                 270

Arg Asp Ser Leu Glu Phe Arg Glu Ile Gly Glu Leu Tyr Leu Pro Lys
        275                 280                 285

Phe Ser Ile Ser Arg Asp Tyr Asn Leu Asn Asp Ile Leu Leu Gln Leu
290                 295                 300

Gly Ile Glu Glu Ala Phe Thr Ser Lys Ala Asp Leu Ser Gly Ile Thr
305                 310                 315                 320

Gly Ala Arg Asn Leu Ala Val Ser Gln Val Val His Lys Ala Val Leu
                325                 330                 335

Asp Val Phe Glu Glu Gly Thr Glu Ala Ser Ala Ala Thr Ala Val Lys
            340                 345                 350

Ile Thr Arg Arg Ser Ile Asp Val Glu Thr Thr Ile Val Arg Phe
        355                 360                 365

Asn Arg Pro Phe Leu Met Ile Ile Val Pro Thr Asp Thr Gln Asn Ile
370                 375                 380

Phe Phe Met Ser Lys Val Thr Asn Pro Lys Gln Ala
385                 390                 395                 400

405                 410

<210> SEQ ID NO 5
<211> LENGTH: 1239
<212> TYPE: DNA
<213> ORGANISM: Artificial
<220> FEATURE:
<223> OTHER INFORMATION: synthetic sequence

<400> SEQUENCE: 5
atgagaggat cccatcacca tcaccatcac tctagacacc ctaacagccc acttgacgag    60
gagaatctga cccaggagaa ccaagaccga gggacacacg tggacctcgg attagcctcc   120

```
gccaacgtgg acttcgcttt cagcctgtac aagcagttag tcctgaaggc ccctgataag    180
aatgtcatct tctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgacttcag     480
gactcagctg cagctaagaa gctcatcaac gactacgtga agaatggaac tagggggaaa    540
atcacagatc tgatcaagga ccttgactcg cagacaatga tggtcctggt gaattacatc    600
ttctttaaag ccaaatggga gatgcccttt gacccccaag atactcatca gtcaaggttc    660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa agttttccat ctcgagggac tataacctga acgacatact tctccagctg    960
ggcattgagg aagccttcac cagcaaggct gacctgtcag ggatcacagg gccaggaac    1020
ctagcagtct cccaggtggt ccataaggct gtgcttgatg tatttgagga gggcacagaa    1080
gcatctgctg ccaccgcggt caaaatcagg gggagatctg agttagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 6
<211> LENGTH: 412
<212> TYPE: PRT
<213> ORGANISM: Artificial
<220> FEATURE:
<223> OTHER INFORMATION: synthetic sequence

<400> SEQUENCE: 6

```
Met Arg Gly Ser His His His His His Ser Arg His Pro Asn Ser
1               5                  10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
```

|   |   |   | 165 |   |   |   | 170 |   |   |   | 175 |   |
|---|---|---|---|---|---|---|---|---|---|---|---|---|

Thr Arg Gly Lys Ile Thr Asp Leu Ile Lys Asp Leu Asp Ser Gln Thr
              180                        185                     190

Met Met Val Leu Val Asn Tyr Ile Phe Phe Lys Ala Lys Trp Glu Met
         195                        200                   205

Pro Phe Asp Pro Gln Asp Thr His Gln Ser Arg Phe Tyr Leu Ser Lys
     210                          215                        220

Lys Lys Trp Val Met Val Pro Met Met Ser Leu His His Leu Thr Ile
225                   230                     235                 240

Pro Tyr Phe Arg Asp Glu Glu Leu Ser Cys Thr Val Val Glu Leu Lys
            245                     250                   255

Tyr Thr Gly Asn Ala Ser Ala Leu Phe Ile Leu Pro Asp Gln Asp Lys
         260                        265                   270

Met Glu Glu Val Glu Ala Met Leu Leu Pro Glu Thr Leu Lys Arg Trp
         275                      280                 285

Arg Asp Ser Leu Glu Phe Arg Glu Ile Gly Glu Leu Tyr Leu Pro Lys
     290                         295                     300

Phe Ser Ile Ser Arg Asp Tyr Asn Leu Asn Asp Ile Leu Leu Gln Leu
305                   310                     315                 320

Gly Ile Glu Glu Ala Phe Thr Ser Lys Ala Asp Leu Ser Gly Ile Thr
            325                     330                   335

Gly Ala Arg Asn Leu Ala Val Ser Gln Val Val His Lys Ala Val Leu
         340                        345                   350

Asp Val Phe Glu Glu Gly Thr Glu Ala Ser Ala Ala Thr Ala Val Lys
         355                      360                 365

Ile Arg Gly Arg Ser Glu Leu Val Glu Thr Arg Thr Ile Val Arg Phe
     370                         375                     380

Asn Arg Pro Phe Leu Met Ile Ile Val Pro Thr Asp Thr Gln Asn Ile
385                   390                     395                 400

Phe Phe Met Ser Lys Val Thr Asn Pro Lys Gln Ala
         405                      410

<210> SEQ ID NO 7
<211> LENGTH: 1239
<212> TYPE: DNA
<213> ORGANISM: Artificial
<220> FEATURE:
<223> OTHER INFORMATION: synthetic sequence

<400> SEQUENCE: 7

```
atgagaggat cccatcacca tcaccatcac tctagacacc ctaacagccc acttgacgag    60
gagaatctga cccaggagaa ccaagaccga gggacacacg tggacctcgg attagcctcc   120
gccaacgtgg acttcgcttt cagcctgtac aagcagttag tcctgaaggc ccctgataag   180
aatgtcatct tctccccact gagcatctcc accgccttgg ccttcctgtc tctggggggcc   240
cataatacca ccctgacaga gattctcaaa ggcctcaagt caacctcac ggagacttct   300
gaggcagaaa ttcaccagag cttccagcac tcctgcgca ccctcaatca gtccagcgat   360
gagctgcagc tgagtatggg aaatgccatg tttgtcaaag agcaactcag tctgctggac   420
aggttcacgg aggatgccaa gaggctgtat ggctccgagg cctttgccac tgactttcag   480
gactcagctg cagctaagaa gctcatcaac gactacgtga agaatggaac tagggggaaa   540
atcacagatc tgatcaagga ccttgactcg cagacaatga tggtcctggt gaattacatc   600
ttctttaaag ccaaatggga gatgcccttt gaccccaag atactcatca gtcaaggttc   660
```

```
tacttgagca agaaaaagtg ggtaatggtg cccatgatga gtttgcatca cctgactata      720
ccttacttcc gggacgagga gctgtcctgc accgtggtgg agctgaagta cacaggcaat      780
gccagcgcac tcttcatcct ccctgatcaa gacaagatgg aggaagtgga agccatgctg      840
ctcccagaga ccctgaagcg gtggagagac tctctggagt tcagagagat aggtgagctc      900
tacctgccaa agttttccat ctcgagggac tataacctga cgacatact tctccagctg       960 ggcattgagg aagccttcac cagcaaggct gacctgtcag ggatcacagg gccaggaac      1020 ctagcagtct cccaggtggt ccataaggct gtgcttgatg tatttgagga gggcacagaa     1080
gcatctgctg ccaccgcggt caaaatcaag cttagaacaa cattagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

```
<210> SEQ ID NO 8
<211> LENGTH: 412
<212> TYPE: PRT
<213> ORGANISM: Artificial
<220> FEATURE:
<223> OTHER INFORMATION: synthetic sequence

<400> SEQUENCE: 8
```

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
```

```
                260               265               270
Met Glu Glu Val Glu Ala Met Leu Leu Pro Glu Thr Leu Lys Arg Trp
                    275               280               285

Arg Asp Ser Leu Glu Phe Arg Glu Ile Gly Glu Leu Tyr Leu Pro Lys
            290               295               300

Phe Ser Ile Ser Arg Asp Tyr Asn Leu Asn Asp Ile Leu Leu Gln Leu
305             310               315               320

Gly Ile Glu Glu Ala Phe Thr Ser Lys Ala Asp Leu Ser Gly Ile Thr
                325               330               335

Gly Ala Arg Asn Leu Ala Val Ser Gln Val Val His Lys Ala Val Leu
            340               345               350

Asp Val Phe Glu Glu Gly Thr Glu Ala Ser Ala Ala Thr Ala Val Lys
                355               360               365

Ile Lys Leu Arg Thr Thr Leu Val Glu Thr Arg Thr Ile Val Arg Phe
            370               375               380

Asn Arg Pro Phe Leu Met Ile Ile Val Pro Thr Asp Thr Gln Asn Ile
385             390               395               400

Phe Phe Met Ser Lys Val Thr Asn Pro Lys Gln Ala
                405               410
```

```
<210> SEQ ID NO 9
<211> LENGTH: 1239
<212> TYPE: DNA
<213> ORGANISM: Artificial
<220> FEATURE:
<223> OTHER INFORMATION: synthetic sequence

<400> SEQUENCE: 9
atgagaggat cccatcacca tcaccatcac tctagacacc ctaacagccc acttgacgag     60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct tctccccact gagcatctcc accgccttgg ccttcctgtc tctgggggcc    240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac taggggaaa     540
atcacagatc tgatcaagga ccttgactcg cagacaatga tggtcctggt gaattacatc    600
ttctttaaag ccaaatggga gatgcccttt gaccccaag atactcatca gtcaaggttc     660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt cagagagat aggtgagctc    900
tacctgccaa agttttccat ctcgagggac tataacctga cgacatact tctccagctg     960
ggcattgagg aagccttcac cagcaaggct gacctgtcag ggatcacagg ggccaggaac   1020
ctagcagtct cccaggtggt ccataaggct gtgcttgatg tatttgagga gggcacagaa   1080
gcatctgctg ccaccgcggt caaaatcatg acaagatcta acgcagtgga gacgcgtacc   1140
attgtgcgtt tcaacaggcc cttcctgatg atcattgtcc ctacagacac ccagaacatc   1200
```
ttcttcatga gcaaagtcac caatcccaag caagcctaa                    1239

<210> SEQ ID NO 10
<211> LENGTH: 412
<212> TYPE: PRT
<213> ORGANISM: Artificial
<220> FEATURE:
<223> OTHER INFORMATION: synthetic sequence

<400> SEQUENCE: 10

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
            35                  40                  45

Leu Tyr Lys Gln Leu Val Leu Lys Ala Pro Asp Lys Asn Val Ile Phe
        50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
```

```
            355                 360                 365
Ile Met Thr Arg Ser Asn Ala Val Glu Thr Arg Thr Ile Val Arg Phe
        370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

<210> SEQ ID NO 11
<211> LENGTH: 1239
<212> TYPE: DNA
<213> ORGANISM: Artificial
<220> FEATURE:
<223> OTHER INFORMATION: synthetic sequence

<400> SEQUENCE: 11

```
atgagaggat cccatcacca tcaccatcac tctagacacc ctaacagccc acttgacgag      60
gagaatctga cccaggagaa ccaagaccga gggacacacg tggacctcgg attagcctcc    120
gccaacgtgg acttcgcttt cagcctgtac aagcagttag tcctgaaggc ccctgataag    180
aatgtcatct ctccccact gagcatctcc accgccttgg ccttcctgtc tctgggggcc     240
cataatacca ccctgacaga gattctcaaa ggcctcaagt tcaacctcac ggagacttct    300
gaggcagaaa ttcaccagag cttccagcac ctcctgcgca ccctcaatca gtccagcgat    360
gagctgcagc tgagtatggg aaatgccatg tttgtcaaag agcaactcag tctgctggac    420
aggttcacgg aggatgccaa gaggctgtat ggctccgagg cctttgccac tgactttcag    480
gactcagctg cagctaagaa gctcatcaac gactacgtga agaatggaac taggggggaaa   540
atcacagatc tgatcaagga ccttgactcg cagacaatga tggtcctggt gaattacatc    600
ttctttaaag ccaaatggga tgcccttt gaccccaag atactcatca gtcaaggttc       660
tacttgagca agaaaaagtg ggtaatggtg cccatgatga gtttgcatca cctgactata    720
ccttacttcc gggacgagga gctgtcctgc accgtggtgg agctgaagta cacaggcaat    780
gccagcgcac tcttcatcct ccctgatcaa gacaagatgg aggaagtgga agccatgctg    840
ctcccagaga ccctgaagcg gtggagagac tctctggagt tcagagagat aggtgagctc    900
tacctgccaa gttttccat ctcgagggac tataacctga acgacatact tctccagctg     960
ggcattgagg aagcccttca cagcaaggct gacctgtcag ggatcacagg gccaggaac    1020
ctagcagtct cccaggtggt ccataaggct gtgcttgatg tatttgagga gggcacagaa   1080
gcatctgctg ccaccgcggt caaaatcacc gagcgtgtct cgcccgtgga gacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 12
<211> LENGTH: 412
<212> TYPE: PRT
<213> ORGANISM: Artificial
<220> FEATURE:
<223> OTHER INFORMATION: synthetic sequence

<400> SEQUENCE: 12

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30
```

-continued

His Val Asp Leu Gly Leu Ala Ser Ala Asn Val Asp Phe Ala Phe Ser
         35                  40                  45

Leu Tyr Lys Gln Leu Val Leu Lys Ala Pro Asp Lys Asn Val Ile Phe
 50                  55                  60

Ser Pro Leu Ser Ile Ser Thr Ala Leu Ala Phe Leu Ser Leu Gly Ala
 65                  70                  75                  80

His Asn Thr Thr Leu Thr Glu Ile Leu Lys Gly Leu Lys Phe Asn Leu
                 85                  90                  95

Thr Glu Thr Ser Glu Ala Glu Ile His Gln Ser Phe Gln His Leu Leu
                100                 105                 110

Arg Thr Leu Asn Gln Ser Ser Asp Glu Leu Gln Leu Ser Met Gly Asn
            115                 120                 125

Ala Met Phe Val Lys Glu Gln Leu Ser Leu Leu Asp Arg Phe Thr Glu
130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Glu Arg Val Ser Pro Val Glu Thr Arg Thr Ile Val Arg Phe
370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 13
<211> LENGTH: 1239
<212> TYPE: DNA
<213> ORGANISM: Artificial
<220> FEATURE:
<223> OTHER INFORMATION: synthetic sequence

<400> SEQUENCE: 13

```
atgagaggat cccatcacca tcaccatcac tctagacacc ctaacagccc acttgacgag      60
gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct ctccccact gagcatctcc accgccttgg ccttcctgtc tctgggggcc      240
cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggaaa      540
atcacagatc tgatcaagga ccttgactcg cagacaatga tggtcctggt gaattacatc     600
ttctttaaag ccaaatggga gatgcccttt gaccccaag atactcatca gtcaaggttc      660
tacttgagca agaaaagtg ggtaatggtg cccatgatga gtttgcatca cctgactata      720
ccttacttcc gggacgagga gctgtcctgc accgtggtgg agctgaagta cacaggcaat     780
gccagcgcac tcttcatcct ccctgatcaa gacaagatgg aggaagtgga agccatgctg     840
ctcccagaga ccctgaagcg gtggagagac tctctggagt tcagagagat aggtgagctc     900
tacctgccaa gttttccat ctcgagggac tataacctga cgacatact ctccagctg        960
ggcattgagg aagccttcac cagcaaggct gacctgtcag ggatcacagg gccaggaac     1020
ctagcagtct cccaggtggt ccataaggct gtgcttgatg tatttgagga gggcacagaa    1080
gcatctgctg ccaccgcggt caaaatcacc tttagatctg cattagtgga gacgcgtacc    1140
attgtgcgtt tcaacaggcc cttcctgatg atcattgtcc ctacagacac ccagaacatc    1200
ttcttcatga gcaaagtcac caatcccaag caagcctaa                           1239
```

<210> SEQ ID NO 14
<211> LENGTH: 412
<212> TYPE: PRT
<213> ORGANISM: Artificial
<220> FEATURE:
<223> OTHER INFORMATION: synthetic sequence

<400> SEQUENCE: 14

```
Met Arg Gly Ser His His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125
```

```
Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Lys Lys Leu Ile Asn Asp Tyr Val Lys Asn Gly
            165                 170                 175

Thr Arg Gly Lys Ile Thr Asp Leu Ile Lys Asp Leu Asp Ser Gln Thr
                180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
        260                 265                 270

Met Glu Glu Val Glu Ala Met Leu Leu Pro Glu Thr Leu Lys Arg Trp
    275                 280                 285

Arg Asp Ser Leu Glu Phe Arg Glu Ile Gly Glu Leu Tyr Leu Pro Lys
290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
                325                 330                 335

Gly Ala Arg Asn Leu Ala Val Ser Gln Val Val His Lys Ala Val Leu
            340                 345                 350

Asp Val Phe Glu Glu Gly Thr Glu Ala Ser Ala Ala Thr Ala Val Lys
        355                 360                 365

Ile Thr Phe Arg Ser Ala Leu Val Glu Thr Arg Thr Ile Val Arg Phe
    370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410
```

<210> SEQ ID NO 15
<211> LENGTH: 1206
<212> TYPE: DNA
<213> ORGANISM: Artificial
<220> FEATURE:
<223> OTHER INFORMATION: synthetic sequence

<400> SEQUENCE: 15

```
atgcatccga acagcccgct ggatgaagaa aacctgaccc aggaaaacca ggatcgcggc      60
acccatgtgg atctgggtct ggccagcgcg aacgtggatt ttgcgttcag cctgtataaa     120
cagctggtgc tgaaagcgcc ggataaaaac gtgatttta gcccgctgtc tattagcacc     180
gcgctggcct ttctgagcct gggcgcgcat aacaccaccc tgaccgaaat tctgaaaggc     240
ctgaaattta acctgaccga aaccagcgaa gcggaaattc atcagagctt tcagcatctg     300
ctgcgtaccc tgaaccagag cagcgatgaa ctgcagctgt ctatgggcaa cgcgatgttt     360
gtgaaagaac agcgtctctc tgctggatcgt tttaccgaag atgcgaaacg tctgtatggc     420
agcgaagcgt ttgcgaccga ttttcaggat agcgcggcgg cgaaaaaact gattaacgat     480
```

```
tatgtgaaaa acggcacccg tggcaaaatt accgatctga tcaaagatct ggatagccag    540
accatgatgg tgctggtgaa ctacatcttc ttcaaagcga atgggaaat gccgtttgat     600 ccgcaggata cccatcagag ccgttttac ctgagcaaaa aaaatgggt gatggtgccg     660 atgatgagcc tgcatcatct gaccattccg tatttcgtg atgaagaact gagctgcacc    720
gtggtggaac tgaaatatac cggcaacgcg agcgcgctgt ttattctgcc ggatcaggat   780
aaaatggaag aagtggaagc gatgctgctg ccggaaaccc tgaaacgttg gcgtgatagc   840
ctggaatttc gtgaaattgg cgaactgtat ctgccgaaat ttagcattag ccgcgattat   900
aacctgaacg atattctgct gcagctgggc attgaagaag cgtttaccag caaagcggat   960
ctgagcggca ttaccggtgc gcgtaacctg ccgtgagcc aggtggtgca taaagcggtg   1020
ctggatgtgt ttgaagaagg caccgaagcg agcgcggcga ccgcggtgaa aattaaactg   1080
cgtaccaccc tggtggaaac ccgtaccatt gtgcgtttta accgtccgtt tctgatgatt   1140
attgtgccga ccgataccca gaacatcttt ttcatgagca aagtgaccaa tccgaaacag   1200
gcgtaa                                                              1206
```

<210> SEQ ID NO 16
<211> LENGTH: 401
<212> TYPE: PRT
<213> ORGANISM: Artificial
<220> FEATURE:
<223> OTHER INFORMATION: synthetic sequence

<400> SEQUENCE: 16

```
Met His Pro Asn Ser Pro Leu Asp Glu Glu Asn Leu Thr Gln Glu Asn
1               5                   10                  15

Gln Asp Arg Gly Thr His Val Asp Leu Gly Leu Ala Ser Ala Asn Val
            20                  25                  30

Asp Phe Ala Phe Ser Leu Tyr Lys Gln Leu Val Leu Lys Ala Pro Asp
        35                  40                  45

Lys Asn Val Ile Phe Ser Pro Leu Ser Ile Ser Thr Ala Leu Ala Phe
    50                  55                  60

Leu Ser Leu Gly Ala His Asn Thr Thr Leu Thr Glu Ile Leu Lys Gly
65                  70                  75                  80

Leu Lys Phe Asn Leu Thr Glu Thr Ser Glu Ala Glu Ile His Gln Ser
                85                  90                  95

Phe Gln His Leu Leu Arg Thr Leu Asn Gln Ser Ser Asp Glu Leu Gln
            100                 105                 110

Leu Ser Met Gly Asn Ala Met Phe Val Lys Glu Gln Leu Ser Leu Leu
        115                 120                 125

Asp Arg Phe Thr Glu Asp Ala Lys Arg Leu Tyr Gly Ser Glu Ala Phe
    130                 135                 140

Ala Thr Asp Phe Gln Asp Ser Ala Ala Ala Lys Lys Leu Ile Asn Asp
145                 150                 155                 160

Tyr Val Lys Asn Gly Thr Arg Gly Lys Ile Thr Asp Leu Ile Lys Asp
                165                 170                 175

Leu Asp Ser Gln Thr Met Met Val Leu Val Asn Tyr Ile Phe Phe Lys
            180                 185                 190

Ala Lys Trp Glu Met Pro Phe Asp Pro Gln Asp Thr His Gln Ser Arg
        195                 200                 205

Phe Tyr Leu Ser Lys Lys Lys Trp Val Met Val Pro Met Met Ser Leu
    210                 215                 220
```

His His Leu Thr Ile Pro Tyr Phe Arg Asp Glu Leu Ser Cys Thr
225                 230                 235                 240

Val Val Glu Leu Lys Tyr Thr Gly Asn Ala Ser Ala Leu Phe Ile Leu
            245                 250                 255

Pro Asp Gln Asp Lys Met Glu Glu Val Glu Ala Met Leu Leu Pro Glu
                260                 265                 270

Thr Leu Lys Arg Trp Arg Asp Ser Leu Glu Phe Arg Glu Ile Gly Glu
            275                 280                 285

Leu Tyr Leu Pro Lys Phe Ser Ile Ser Arg Asp Tyr Asn Leu Asn Asp
            290                 295                 300

Ile Leu Leu Gln Leu Gly Ile Glu Glu Ala Phe Thr Ser Lys Ala Asp
305                 310                 315                 320

Leu Ser Gly Ile Thr Gly Ala Arg Asn Leu Ala Val Ser Gln Val Val
                325                 330                 335

His Lys Ala Val Leu Asp Val Phe Glu Glu Gly Thr Glu Ala Ser Ala
                340                 345                 350

Ala Thr Ala Val Lys Ile Lys Leu Arg Thr Thr Leu Val Glu Thr Arg
            355                 360                 365

Thr Ile Val Arg Phe Asn Arg Pro Phe Leu Met Ile Ile Val Pro Thr
370                 375                 380

Asp Thr Gln Asn Ile Phe Phe Met Ser Lys Val Thr Asn Pro Lys Gln
385                 390                 395                 400

Ala

<210> SEQ ID NO 17
<211> LENGTH: 1239
<212> TYPE: DNA
<213> ORGANISM: Artificial
<220> FEATURE:
<223> OTHER INFORMATION: synthetic sequence

<400> SEQUENCE: 17
atgagaggat cccatcacca tcaccatcac tctagacacc taacagccc acttgacgag       60 gagaatctga cccaggagaa ccaagaccga gggacacacg tggacctcgg attagcctcc     120
gccaacgtgg acttcgcttt cagcctgtac aagcagttag tcctgaaggc ccctgataag     180
aatgtcatct ctccccact gagcatctcc accgccttgg ccttcctgtc tctggggggcc     240 cataatacca ccctgacaga gattctcaaa ggcctcaagt tcaacctcac ggagacttct     300
gaggcagaaa ttcaccagag cttccagcac ctcctgcgca ccctcaatca gtccagcgat     360
gagctgcagc tgagtatggg aaatgccatg tttgtcaaag agcaactcag tctgctggac     420
aggttcacgg aggatgccaa gaggctgtat ggctccgagg cctttgccac tgactttcag     480
gactcagctg cagctaagaa gctcatcaac gactacgtga agaatggaac taggggaaa     540 atcacagatc tgatcaagga ccttgactcg cagacaatga tggtcctggt gaattacatc     600
ttctttaaag ccaaatggga gatgccccttt gacccccaag atactcatca gtcaaggttc     660
tacttgagca agaaaaagtg ggtaatggtg cccatgatga gtttgcatca cctgactata     720
ccttacttcc gggacgagga gctgtcctgc accgtggtgg agctgaagta cacaggcaat     780
gccagcgcac tcttcatcct ccctgatcaa gacaagatga ggaagtggaa agccatgctg     840
ctcccagaga ccctgaagcg gtggagagac tctctggagt tcagagagat aggtgagctc     900
tacctgccaa agttttccat ctcgagggac tataacctga cgacatact tctccagctg     960 ggcattgagg aagccttcac cagcaaggct gacctgtcag gatcacagg ggccaggaac    1020

```
ctagcagtct cccaggtggt ccataaggct gtgcttgatg tatttgagga gggcacagaa   1080
gcatctgctg ccaccgcggt caaaaccgtt gactacgctg ctctggtgga dacgcgtacc   1140
attgtgcgtt tcaacaggcc cttcctgatg atcattgtcc ctacagacac ccagaacatc   1200
ttcttcatga gcaaagtcac caatcccaag caagcctaa                          1239
```

<210> SEQ ID NO 18
<211> LENGTH: 412
<212> TYPE: PRT
<213> ORGANISM: Artificial
<220> FEATURE:
<223> OTHER INFORMATION: synthetic sequence

<400> SEQUENCE: 18

```
Met Arg Gly Ser His His His His His Ser Arg His Pro Asn Ser
1               5                   10                  15

Pro Leu Asp Glu Glu Asn Leu Thr Gln Glu Asn Gln Asp Arg Gly Thr
            20                  25                  30

His Val Asp Leu Gly Leu Ala Ser Ala Asn Val Asp Phe Ala Phe Ser
        35                  40                  45

Leu Tyr Lys Gln Leu Val Leu Lys Ala Pro Asp Lys Asn Val Ile Phe
    50                  55                  60

Ser Pro Leu Ser Ile Ser Thr Ala Leu Ala Phe Leu Ser Leu Gly Ala
65                  70                  75                  80

His Asn Thr Thr Leu Thr Glu Ile Leu Lys Gly Leu Lys Phe Asn Leu
                85                  90                  95

Thr Glu Thr Ser Glu Ala Glu Ile His Gln Ser Phe Gln His Leu Leu
            100                 105                 110

Arg Thr Leu Asn Gln Ser Ser Asp Glu Leu Gln Leu Ser Met Gly Asn
        115                 120                 125

Ala Met Phe Val Lys Glu Gln Leu Ser Leu Leu Asp Arg Phe Thr Glu
    130                 135                 140

Asp Ala Lys Arg Leu Tyr Gly Ser Glu Ala Phe Ala Thr Asp Phe Gln
145                 150                 155                 160

Asp Ser Ala Ala Ala Lys Lys Leu Ile Asn Asp Tyr Val Lys Asn Gly
                165                 170                 175

Thr Arg Gly Lys Ile Thr Asp Leu Ile Lys Asp Leu Asp Ser Gln Thr
            180                 185                 190

Met Met Val Leu Val Asn Tyr Ile Phe Phe Lys Ala Lys Trp Glu Met
        195                 200                 205

Pro Phe Asp Pro Gln Asp Thr His Gln Ser Arg Phe Tyr Leu Ser Lys
    210                 215                 220

Lys Lys Trp Val Met Val Pro Met Met Ser Leu His His Leu Thr Ile
225                 230                 235                 240

Pro Tyr Phe Arg Asp Glu Glu Leu Ser Cys Thr Val Val Glu Leu Lys
                245                 250                 255

Tyr Thr Gly Asn Ala Ser Ala Leu Phe Ile Leu Pro Asp Gln Asp Lys
            260                 265                 270

Met Glu Glu Val Glu Ala Met Leu Leu Pro Glu Thr Leu Lys Arg Trp
        275                 280                 285

Arg Asp Ser Leu Glu Phe Arg Glu Ile Gly Glu Leu Tyr Leu Pro Lys
    290                 295                 300

Phe Ser Ile Ser Arg Asp Tyr Asn Leu Asn Asp Ile Leu Leu Gln Leu
305                 310                 315                 320

Gly Ile Glu Glu Ala Phe Thr Ser Lys Ala Asp Leu Ser Gly Ile Thr
```

-continued

```
                    325                 330                 335

Gly Ala Arg Asn Leu Ala Val Ser Gln Val His Lys Ala Val Leu
                340                 345                 350

Asp Val Phe Glu Glu Gly Thr Glu Ala Ser Ala Ala Thr Ala Val Lys
            355                 360                 365

Thr Val Asp Tyr Ala Ala Leu Val Glu Thr Arg Thr Ile Val Arg Phe
        370                 375                 380

Asn Arg Pro Phe Leu Met Ile Ile Val Pro Thr Asp Thr Gln Asn Ile
385                 390                 395                 400

Phe Phe Met Ser Lys Val Thr Asn Pro Lys Gln Ala
                405                 410

<210> SEQ ID NO 19
<211> LENGTH: 20
<212> TYPE: PRT
<213> ORGANISM: Homo sapiens

<400> SEQUENCE: 19

Gly Thr Glu Ala Ala Gly Ala Met Phe Leu Glu Ala Ile Pro Met Ser
1               5                   10                  15

Ile Pro Pro Glu
            20

<210> SEQ ID NO 20
<211> LENGTH: 20
<212> TYPE: PRT
<213> ORGANISM: Homo sapiens

<400> SEQUENCE: 20

Gly Thr Glu Ala Thr Gly Ala Pro His Leu Glu Glu Lys Ala Trp Ser
1               5                   10                  15

Lys Tyr Gln Thr
            20

<210> SEQ ID NO 21
<211> LENGTH: 20
<212> TYPE: PRT
<213> ORGANISM: Homo sapiens

<400> SEQUENCE: 21

Gly Val Glu Ala Ala Ala Ala Thr Ser Ile Ala Met Ser Arg Met Ser
1               5                   10                  15

Leu Ser Ser Phe
            20

<210> SEQ ID NO 22
<211> LENGTH: 20
<212> TYPE: PRT
<213> ORGANISM: Homo sapiens

<400> SEQUENCE: 22

Gly Thr Glu Ala Ser Ala Ala Thr Ala Val Lys Ile Thr Leu Leu Ser
1               5                   10                  15

Ala Leu Val Glu
            20

<210> SEQ ID NO 23
<211> LENGTH: 20
<212> TYPE: PRT
<213> ORGANISM: Homo sapiens
```

```
<400> SEQUENCE: 23

Gly Ser Glu Ala Ala Ser Thr Ala Val Val Ile Ala Gly Arg Ser
1               5                   10                  15

Leu Asn Pro Asn
            20

<210> SEQ ID NO 24
<211> LENGTH: 20
<212> TYPE: PRT
<213> ORGANISM: Homo sapiens

<400> SEQUENCE: 24

Gly Thr Glu Ala Ala Gly Ser Gly Ser Glu Ile Asp Ile Arg Ile
1               5                   10                  15

Arg Val Pro Ser
            20

<210> SEQ ID NO 25
<211> LENGTH: 20
<212> TYPE: PRT
<213> ORGANISM: Homo sapiens

<400> SEQUENCE: 25

Gly Asn Pro Phe Asp Gln Asp Ile Tyr Gly Arg Glu Glu Leu Arg Ser
1               5                   10                  15

Pro Lys Leu Phe
            20

<210> SEQ ID NO 26
<211> LENGTH: 20
<212> TYPE: PRT
<213> ORGANISM: Homo sapiens

<400> SEQUENCE: 26

Gly Thr Lys Ala Ser Ala Ala Thr Thr Ala Ile Leu Ile Ala Arg Ser
1               5                   10                  15

Ser Pro Pro Trp
            20

<210> SEQ ID NO 27
<211> LENGTH: 20
<212> TYPE: PRT
<213> ORGANISM: Homo sapiens

<400> SEQUENCE: 27

Gly Thr Gln Ala Thr Thr Val Thr Val Gly Phe Met Pro Leu Ser
1               5                   10                  15

Thr Gln Val Arg
            20

<210> SEQ ID NO 28
<211> LENGTH: 20
<212> TYPE: PRT
<213> ORGANISM: Homo sapiens

<400> SEQUENCE: 28

Gly Val Glu Ala Ala Ala Ser Ala Ile Ser Val Ala Arg Thr Leu
1               5                   10                  15

Leu Val Phe Glu
            20
```

```
<210> SEQ ID NO 29
<211> LENGTH: 20
<212> TYPE: PRT
<213> ORGANISM: Homo sapiens

<400> SEQUENCE: 29

Gly Thr Glu Ala Ala Ala Thr Ala Gly Ile Ala Thr Phe Cys Met
1               5                   10                  15

Leu Met Pro Glu
            20

<210> SEQ ID NO 30
<211> LENGTH: 20
<212> TYPE: PRT
<213> ORGANISM: Homo sapiens

<400> SEQUENCE: 30

Gly Thr Arg Ala Ala Ala Ala Thr Gly Thr Ile Phe Thr Phe Arg Ser
1               5                   10                  15

Ala Arg Leu Asn
            20

<210> SEQ ID NO 31
<211> LENGTH: 20
<212> TYPE: PRT
<213> ORGANISM: Homo sapiens

<400> SEQUENCE: 31

Gly Thr Glu Ala Ala Ala Ala Thr Thr Phe Ala Ile Lys Phe Phe Ser
1               5                   10                  15

Ala Gln Thr Asn
            20

<210> SEQ ID NO 32
<211> LENGTH: 20
<212> TYPE: PRT
<213> ORGANISM: Homo sapiens

<400> SEQUENCE: 32

Gly Gly Asp Ser Ile Glu Val Pro Gly Ala Arg Ile Leu Gln His Lys
1               5                   10                  15

Asp Glu Leu Asn
            20

<210> SEQ ID NO 33
<211> LENGTH: 20
<212> TYPE: PRT
<213> ORGANISM: Homo sapiens

<400> SEQUENCE: 33

Gly Ser Glu Ala Ala Ala Val Ser Gly Met Ile Ala Ile Ser Arg Met
1               5                   10                  15

Ala Val Leu Tyr
            20

<210> SEQ ID NO 34
<211> LENGTH: 20
<212> TYPE: PRT
<213> ORGANISM: Homo sapiens

<400> SEQUENCE: 34

Gly Thr Val Ala Ser Ser Ser Thr Ala Val Ile Val Ser Ala Arg Met
1               5                   10                  15
```

```
Ala Pro Glu Glu
            20

<210> SEQ ID NO 35
<211> LENGTH: 20
<212> TYPE: PRT
<213> ORGANISM: Homo sapiens

<400> SEQUENCE: 35

Gly Thr Glu Ala Ala Ala Gly Thr Gly Gly Val Met Thr Gly Arg Thr
1               5                   10                  15

Gly His Gly Gly
            20

<210> SEQ ID NO 36
<211> LENGTH: 20
<212> TYPE: PRT
<213> ORGANISM: Homo sapiens

<400> SEQUENCE: 36

Gly Ala Gly Thr Thr Pro Ser Pro Gly Leu Gln Pro Ala His Leu Thr
1               5                   10                  15

Phe Pro Leu Asp
            20

<210> SEQ ID NO 37
<211> LENGTH: 20
<212> TYPE: PRT
<213> ORGANISM: Homo sapiens

<400> SEQUENCE: 37

Gly Thr Glu Ala Ala Ala Ala Thr Ala Ala Ile Met Met Met Arg Cys
1               5                   10                  15

Ala Arg Phe Val
            20

<210> SEQ ID NO 38
<211> LENGTH: 20
<212> TYPE: PRT
<213> ORGANISM: Homo sapiens

<400> SEQUENCE: 38

Gly Thr Glu Ala Ala Ala Ala Thr Ala Val Val Arg Asn Ser Arg Cys
1               5                   10                  15

Ser Arg Met Glu
            20

<210> SEQ ID NO 39
<211> LENGTH: 20
<212> TYPE: PRT
<213> ORGANISM: Homo sapiens

<400> SEQUENCE: 39

Gly Thr Glu Ala Ala Ala Ala Ser Ser Cys Phe Val Val Ala Glu Cys
1               5                   10                  15

Cys Met Glu Ser
            20

<210> SEQ ID NO 40
<211> LENGTH: 20
<212> TYPE: PRT
<213> ORGANISM: Homo sapiens
```

<400> SEQUENCE: 40

Gly Ala Glu Ala Ala Ala Ala Thr Ala Val Val Gly Phe Gly Ser Ser
1               5                   10                  15

Pro Ala Ser Thr
            20

<210> SEQ ID NO 41
<211> LENGTH: 20
<212> TYPE: PRT
<213> ORGANISM: Homo sapiens

<400> SEQUENCE: 41

Gly Val Glu Ala Ala Ala Ala Thr Ala Val Val Val Val Glu Leu Ser
1               5                   10                  15

Ser Pro Ser Thr
            20

<210> SEQ ID NO 42
<211> LENGTH: 20
<212> TYPE: PRT
<213> ORGANISM: Homo sapiens

<400> SEQUENCE: 42

Gly Thr Glu Ala Ala Ala Val Pro Glu Val Glu Leu Ser Asp Gln Pro
1               5                   10                  15

Glu Asn Thr Phe
            20

<210> SEQ ID NO 43
<211> LENGTH: 20
<212> TYPE: PRT
<213> ORGANISM: Homo sapiens

<400> SEQUENCE: 43

Gly Thr Glu Ala Thr Ala Ala Thr Gly Ser Asn Ile Val Glu Lys Gln
1               5                   10                  15

Leu Pro Gln Ser
            20

<210> SEQ ID NO 44
<211> LENGTH: 20
<212> TYPE: PRT
<213> ORGANISM: Homo sapiens

<400> SEQUENCE: 44

Gly Ser Glu Ala Ala Thr Ser Thr Gly Ile His Ile Pro Val Ile Met
1               5                   10                  15

Ser Leu Ala Gln
            20

<210> SEQ ID NO 45
<211> LENGTH: 21
<212> TYPE: DNA
<213> ORGANISM: Artificial Sequence
<220> FEATURE:
<223> OTHER INFORMATION: KLK1 F

<400> SEQUENCE: 45
tggagaacca cacccgccaa g                                       21

<210> SEQ ID NO 46

```
<211> LENGTH: 21
<212> TYPE: DNA
<213> ORGANISM: Artificial Sequence
<220> FEATURE:
<223> OTHER INFORMATION: KLK1R

<400> SEQUENCE: 46
acggcgacag aaggcttatt g                                              21

<210> SEQ ID NO 47
<211> LENGTH: 22
<212> TYPE: DNA
<213> ORGANISM: Artificial Sequence
<220> FEATURE:
<223> OTHER INFORMATION: KLK2F

<400> SEQUENCE: 47
gcctaaagaa gaatagccag gt                                             22

<210> SEQ ID NO 48
<211> LENGTH: 22
<212> TYPE: DNA
<213> ORGANISM: Artificial Sequence
<220> FEATURE:
<223> OTHER INFORMATION: KLK2R

<400> SEQUENCE: 48
ctcagactaa gctctagcac ac                                             22

<210> SEQ ID NO 49
<211> LENGTH: 21
<212> TYPE: DNA
<213> ORGANISM: Artificial Sequence
<220> FEATURE:
<223> OTHER INFORMATION: KLK3F

<400> SEQUENCE: 49
gcatcaggaa caaaagcgtg a                                              21

<210> SEQ ID NO 50
<211> LENGTH: 21
<212> TYPE: DNA
<213> ORGANISM: Artificial Sequence
<220> FEATURE:
<223> OTHER INFORMATION: KLK3R

<400> SEQUENCE: 50
cctgaggaat cgattcttca g                                              21

<210> SEQ ID NO 51
<211> LENGTH: 22
<212> TYPE: DNA
<213> ORGANISM: Artificial Sequence
<220> FEATURE:
<223> OTHER INFORMATION: KLK4F

<400> SEQUENCE: 51
gcggcactgg tcatggaaaa gg                                             22

<210> SEQ ID NO 52
<211> LENGTH: 20
<212> TYPE: DNA
<213> ORGANISM: Artificial Sequence
<220> FEATURE:
<223> OTHER INFORMATION: KLK4R

<400> SEQUENCE: 52
```
caaggccctg caagtacccg                                                  20

<210> SEQ ID NO 53
<211> LENGTH: 20
<212> TYPE: DNA
<213> ORGANISM: Artificial Sequence
<220> FEATURE:
<223> OTHER INFORMATION: KLK5F

<400> SEQUENCE: 53
gagctggggc cggggaagac                                                  20

<210> SEQ ID NO 54
<211> LENGTH: 20
<212> TYPE: DNA
<213> ORGANISM: Artificial Sequence
<220> FEATURE:
<223> OTHER INFORMATION: KLK5R

<400> SEQUENCE: 54
tgggccgggc acaagggtaa                                                  20

<210> SEQ ID NO 55
<211> LENGTH: 18
<212> TYPE: DNA
<213> ORGANISM: Artificial Sequence
<220> FEATURE:
<223> OTHER INFORMATION: KLK6F

<400> SEQUENCE: 55
gagcggccat gaagaagc                                                    18

<210> SEQ ID NO 56
<211> LENGTH: 21
<212> TYPE: DNA
<213> ORGANISM: Artificial Sequence
<220> FEATURE:
<223> OTHER INFORMATION: KLK6R

<400> SEQUENCE: 56
aatcaccatc tgctgtcttg c                                                21

<210> SEQ ID NO 57
<211> LENGTH: 21
<212> TYPE: DNA
<213> ORGANISM: Artificial Sequence
<220> FEATURE:
<223> OTHER INFORMATION: KLK7F

<400> SEQUENCE: 57
gcccagggtg acaagattat t                                                21

<210> SEQ ID NO 58
<211> LENGTH: 20
<212> TYPE: DNA
<213> ORGANISM: Artificial Sequence
<220> FEATURE:
<223> OTHER INFORMATION: KLK7R

<400> SEQUENCE: 58
gtacctctgc acaccaacgg                                                  20

<210> SEQ ID NO 59
<211> LENGTH: 21
<212> TYPE: DNA

<210> SEQ ID NO 59
<211> LENGTH: 21
<212> TYPE: DNA
<213> ORGANISM: Artificial Sequence
<220> FEATURE:
<223> OTHER INFORMATION: KLK8F

<400> SEQUENCE: 59
tactctgtgg cggtgtcctt g                                              21

<210> SEQ ID NO 60
<211> LENGTH: 21
<212> TYPE: DNA
<213> ORGANISM: Artificial Sequence
<220> FEATURE:
<223> OTHER INFORMATION: KLK8R

<400> SEQUENCE: 60
gagccccagg atgtgatgcc c                                              21

<210> SEQ ID NO 61
<211> LENGTH: 21
<212> TYPE: DNA
<213> ORGANISM: Artificial Sequence
<220> FEATURE:
<223> OTHER INFORMATION: KLK9F

<400> SEQUENCE: 61
ggccggcctc ttccacctta c                                              21

<210> SEQ ID NO 62
<211> LENGTH: 20
<212> TYPE: DNA
<213> ORGANISM: Artificial Sequence
<220> FEATURE:
<223> OTHER INFORMATION: KLK9R

<400> SEQUENCE: 62
gcgcgggctc agttctccat                                                20

<210> SEQ ID NO 63
<211> LENGTH: 21
<212> TYPE: DNA
<213> ORGANISM: Artificial Sequence
<220> FEATURE:
<223> OTHER INFORMATION: KLK10F

<400> SEQUENCE: 63
gcggaaacaa gccactgtgg g                                              21

<210> SEQ ID NO 64
<211> LENGTH: 21
<212> TYPE: DNA
<213> ORGANISM: Artificial Sequence
<220> FEATURE:
<223> OTHER INFORMATION: KLK10R

<400> SEQUENCE: 64
ggtaaacacc ccacgagagg a                                              21

<210> SEQ ID NO 65
<211> LENGTH: 20
<212> TYPE: DNA
<213> ORGANISM: Artificial Sequence
<220> FEATURE:
<223> OTHER INFORMATION: KLK11F

<400> SEQUENCE: 65
ccgctacata gttcacctgg                                                20

```
<210> SEQ ID NO 66
<211> LENGTH: 21
<212> TYPE: DNA
<213> ORGANISM: Artificial Sequence
<220> FEATURE:
<223> OTHER INFORMATION: KLK11R

<400> SEQUENCE: 66
aggtgtgagg caggcgtaac t                                              21

<210> SEQ ID NO 67
<211> LENGTH: 21
<212> TYPE: DNA
<213> ORGANISM: Artificial Sequence
<220> FEATURE:
<223> OTHER INFORMATION: KLK12F

<400> SEQUENCE: 67
tggcagacaa agagacaagg t                                              21

<210> SEQ ID NO 68
<211> LENGTH: 20
<212> TYPE: DNA
<213> ORGANISM: Artificial Sequence
<220> FEATURE:
<223> OTHER INFORMATION: KLK12R

<400> SEQUENCE: 68
cttagaaggg ctggcaggag                                                20

<210> SEQ ID NO 69
<211> LENGTH: 24
<212> TYPE: DNA
<213> ORGANISM: Artificial Sequence
<220> FEATURE:
<223> OTHER INFORMATION: KLK13F

<400> SEQUENCE: 69
ctacacctgc ttcccccact ctca                                           24

<210> SEQ ID NO 70
<211> LENGTH: 20
<212> TYPE: DNA
<213> ORGANISM: Artificial Sequence
<220> FEATURE:
<223> OTHER INFORMATION: KLK13R

<400> SEQUENCE: 70
gccggtcagg ttgcccacat                                                20

<210> SEQ ID NO 71
<211> LENGTH: 20
<212> TYPE: DNA
<213> ORGANISM: Artificial Sequence
<220> FEATURE:
<223> OTHER INFORMATION: KLK14F

<400> SEQUENCE: 71
ctgggcaagc acaacctgag                                                20

<210> SEQ ID NO 72
<211> LENGTH: 21
<212> TYPE: DNA
<213> ORGANISM: Artificial Sequence
<220> FEATURE:
```

```
-continued

<223> OTHER INFORMATION: KLK14R

<400> SEQUENCE: 72
gcatcgtttc ctcaatccag c                                              21

<210> SEQ ID NO 73
<211> LENGTH: 20
<212> TYPE: DNA
<213> ORGANISM: Artificial Sequence
<220> FEATURE:
<223> OTHER INFORMATION: KLK15F

<400> SEQUENCE: 73
caagtggctc tctacgagcg                                                20

<210> SEQ ID NO 74
<211> LENGTH: 20
<212> TYPE: DNA
<213> ORGANISM: Artificial Sequence
<220> FEATURE:
<223> OTHER INFORMATION: KLK15R

<400> SEQUENCE: 74
atcacacggg tggtcatgtg                                                20
```

USE OF SERINE PROTEASE INHIBITORS IN THE TREATMENT OF NEUTROPENIA

CROSS-REFERENCE TO RELATED APPLICATIONS

This application is a divisional application of U.S. application Ser. No. 13/256,096, filed on Sep. 12, 2011, which is a National Phase entry of PCT Application No. PCT/IB2010/051038, filed on Mar. 10, 2010, which claims priority under 35 U.S.C. §§119(e), 120 and 365(c) to U.S. Provisional Application No. 61/202,535, filed on Mar. 10, 2009, the entire contents of each of which are incorporated herein by reference in their entirety.

FIELD OF THE INVENTION

The invention relates to therapeutic compounds which are inhibitors of serine proteases, to pharmaceutical compositions thereof and to their use in the treatment of the human or animal body. More specifically, the present invention relates to a method for the treatment of neutropenia comprising the administration to a subject in need thereof of a therapeutically effective amount of a serine protease inhibitor. The invention also comprises prevention of apoptosis of myeloid cells (1) during and after transfection of bone marrow cells performed for gene therapy, (2) during blood stem cell mobilization performed for reconstitution of hematopoiesis and (3) during infusion of cells of the myeloid lineage for reconstitution of hematopoiesis for gene therapy or for treatment of neutropenia by infusion of neutrophils.

REFERENCE TO A SEQUENCE LISTING

This application contains references to amino acid sequences and/or nucleic acid sequences which have been submitted concurrently herewith as the sequence listing text file "2336374_1.txt", file size 58.8 KiloBytes (KB), created on Nov. 24, 2014. The aforementioned sequence listing is hereby incorporated by reference in its entirety pursuant to 37 C.F.R. §1.52(e)(5).

BACKGROUND OF THE INVENTION

The invention relates to the use of compounds which are inhibitors of serine proteases. Proteases or proteolytic enzymes are essential in organisms, from bacteria and viruses to mammals. Proteases digest and degrade proteins by hydrolyzing peptide bonds. Serine proteases (EC. 3.4.21) have common features in the active site, primarily an active serine residue. There are two main types of serine proteases; the chymotrypsin/trypsin/elastase-like and subtilisin-like, which have an identical spatial arrangement of catalytic His, Asp, and Ser but in quite different protein scaffolds. However, over twenty families (S1-S27) of serine proteases have been identified that are grouped into 6 clans on the basis of structural similarity and other functional evidence, SA, SB, SC, SE, SF & SG. Family of chymotrypsin/trypsin/elastase-like serine proteases have been subdivided into two classes. The "large" class (ca 230 residues) includes mostly mammalian enzymes such as trypsin, chymotrypsin, elastase, kallikrein, and thrombin. The "small" class (ca 190 residues) includes the bacterial enzymes.

The catalytic His, Asp and Ser are flanked by substrate amino acid side chain residue binding pockets termed S1', S2', S3' etc on the C-terminal or 'prime' side of the substrate and S1, S2, S3 etc on the N-terminal side. This nomenclature is as described in Structure and Mechanism in Protein Science: A Guide to Enzyme Catalysis and Protein Folding, Alan Fersht, 1999 (W.H. Freeman and Company) pages 40-43 and Brik et al, Org. Biomol. Chem., 2003, 1, 5-14. The chymotrypsin/trypsin/elastase-like serine proteases can also be further subdivided by the residues present in the Si pocket as described in Introduction to Protein Structure, Carl Branden and John Tooze, 1991 (Garland Publishing Inc) pages 231-241. The subdivisions are chymotrypsin-like (Gly-226, Ser-189 and Gly-216 in S1 pocket), trypsin-like (Gly-226, Asp-189 and Gly-216 in S1) and elastase-like (Val-226 and Thr-216 in S1) where the residues numbering is taken from the standard chymotrypsin numbering. The trypsin-like serine proteases prefer substrates which place either Lys or Arg in the S1 pocket.

The serine proteases have a common catalytic mechanism characterized by a particularly reactive Ser residue at position 195 using the chymotrypsin numbering system. Examples of serine proteases include trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase π, subtilisin, urokinase (uPA), Factor VIIa, Factor IXa, and Factor Xa. The serine proteases have been investigated extensively for many years and are a major focus of research as a drug target due to their role in regulating a wide variety of physiological processes.

Processes involving serine proteases include coagulation, fibrinolysis, fertilization, development, malignancy, neuromuscular patterning and inflammation. It is well known that these compounds inhibit a variety of circulating proteases as well as proteases that are activated or released in tissue. It is also known that serine protease inhibitors inhibit critical cellular processes, such as adhesion, migration, free radical production and apoptosis. In addition, animal experiments indicate that intravenously administered serine protease inhibitors, variants or cells expressing serine protease inhibitors, provide protection against tissue damage.

Serine protease inhibitors have also been predicted to have potential beneficial uses in the treatment of disease in a wide variety of clinical areas such as oncology, hematology, neurology, pulmonary medicine, immunology, inflammation and infectious disease. Serine protease inhibitors may also be beneficial in the treatment of thrombotic diseases, asthma, emphysema, cirrhosis, arthritis, carcinoma, melanoma, restenosis, atheroma, trauma, shock and reperfusion injury. A useful review is found in Expert Opin. Ther. Patents (2002), 12(8). Serine protease inhibitors are disclosed in US published patent applications US 2003/0100089 and 2004/0180371 and in U.S. Pat. Nos. 6,784,182, 6,656,911, 6,656,910, 6,608,175, 6,534,495 and 6,472,393.

Leukopenia refers to a decrease in the total leukocyte count below about 4.0×109 cells/L. Usually, the reduction is a result of a decrease in the number of polymorphonuclear neutrophils (PMN) (neutropenia), their numbers being usually less than 2.0×109 cells/L and frequently below 1.0×109 cells/L. Neutropenia may result from viral infections (e.g. influenza, measles, hepatitis virus, chickenpox, dengue and yellow fever, HIV) or from overwhelming bacterial infections including miliary tuberculosis and septicemia. Furthermore, neutropenia develops due to irradiation or treatment with drugs used e.g. in chemotherapy of malignant diseases or vasculitis and autoimmune diseases. Examples for drug-induced neutropenia are sulfonamides, antithyroid drugs, antihistamines, antimicrobial agents, phenothiazines and various analgesics, sedatives and anti-inflammatory agents or various toxic chemicals. Induction of cell death by infectious agents, drugs and toxic chemicals or antibodies may affect neutrophils and/or their precursor cells in the bone marrow. Antibodies to cells of the myeloid lineage are seen in immune mediated diseases such as systemic lupus erythematodes or juvenile rheumatoid arthritis. Last but not least various forms of congenital neutropenia have been described. Neutropenia results not only from damage of PMN in the circulation, but also from damage of stem cells and mitotic cells in the bone marrow by infectious agents, drugs, irradiation and toxic chemicals or due to slowing of cell divisions, blockade of DNA strand duplication, RNA formation or disruption of the microtubules of the mitotic spindle.

Neutropenia e.g. due to chemotherapy for hematologic malignancies, solid tumors or carcinomas leads to an impaired host response with significant morbidity and mortality due to infections. For example chemotherapy of early breast cancer with cyclophosphamide, methotrexate and fluorouracil results in neutropenic events in 30% of the patients with sepsis with requirement for delay of further anti-cancer treatment or dose reduction. Dose reductions of 20-30% have been associated with lower complete response rates and shortened survival in patients with lymphoma or with inferior relapse—free survival. Despite of improvements in antibacterial therapy for neutropenic sepsis, each year approximately 5% of patients receiving myelotoxic chemotherapy die due to infection related complications.

In-vitro handling of neutrophils and their precursor cells e.g. for gene therapy or for preparation of infusions of neutrophils is associated with an increase of cell death due to induction of apoptosis of myeloid cells.

Present agents used for the treatment of neutropenia include G-CSF, GM-CSF and G-CSF conjugated to polyethylene glycol as pegulated G-CSF. Despite the availability and considerable efficacy of the above approved agents in reducing the risk of neutropenia and its complications remain significant issues in oncology. Rarely rupture of the spleen but more frequently increase of the spleen volume, disturbances of gas exchange in the lung and single cases of acute injury stroke and myocardial infarction have been observed in healthy donors receiving G-CSF for harvesting peripheral blood stem cells. The evidences that G-CSF causes myelodysplastic syndromes and acute myeloic leukemia are less clear and need to be analyzed in further prospective long-term studies.

Although these approaches have shown promise, there is a need of improved therapeutic, prophylactic or diagnostic approaches for the treatment of neutropenia. The present invention provides an improved and reliable method for the treatment, diagnosis or prophylaxis of neutropenia comprising the administration to a subject in need thereof of a therapeutically effective amount of a Serine protease inhibitor.

These and other objects as will be apparent from the foregoing have been achieved by the present invention.

SUMMARY OF THE INVENTION

The present invention concerns a method for the treatment or prevention of patients suffering from neutropenia comprising the administration to said patients in need thereof of a therapeutically effective amount of serine protease inhibitors. Preferably the serine protease inhibitors is a Kallikrein inhibitor and preferably said Kallikrein inhibitor is selected amongst hK2, hK3, hK4, hK5, hK6, hK7, hK8, hK9 hK10, hK11, hK12, hK13, hK14, hK15 inhibitors or mixtures thereof. The most preferably said Kallikrein inhibitor is selected among hK2, hK4, hK11, hK5, hK14 inhibitors or mixtures thereof. Even more preferably said Kallikrein inhibitor is an hK2 inhibitor. Preferably the serine protease inhibitors are selected from the group comprising SEQ ID No 2, SEQ ID No 4, SEQ ID No 6, SEQ ID No 8, SEQ ID No 10, SEQ ID No 12, SEQ ID No 14, SEQ ID No 16, SEQ ID No 18 or mixtures thereof.

Also disclosed are serine protease inhibitors for use in a method of treating or preventing neutropenia in patients which develops due to infections, septicemia, chemotherapy, irradiation, toxic chemicals or as side effects of any medication. Preferably, the number and/or activation state of neutrophils is impaired. Said serine protease inhibitors are also for use in a method of treating or preventing skin ulcers in diabetes patients in which neutrophils undergo cell death, or skin ulcers developing in patients with peripheral arterial disease associated with hypoxic conditions in the skin and neutrophil dysfunction and apoptosis.

Also said serine protease inhibitors are for use in a method of treating or preventing irradiation induced damage of myeloid cells as occurs in the course of treatment of malignancy, accidents in nuclear plants or use of nuclear weapons. Preferably said serine protease inhibitors is a Kallikrein inhibitor and preferably said Kallikrein inhibitor is selected amongst hK2, hK3, hK4, hK5, hK6, hK7, hK8, hK9 hK10, hK11, hK12, hK13, hK14, hK15 inhibitors or mixtures thereof Preferably said serine protease inhibitors are selected from the group comprising SEQ ID No 2, SEQ ID No 4, SEQ ID No 6, SEQ ID No 8, SEQ ID No 10, SEQ ID No 12, SEQ ID No 14, SEQ ID No 16, SEQ ID No 18 or mixtures thereof.

Further disclosed are serine protease inhibitors for use in the in-vitro preparation of neutrophils and their bone marrow precursors to perform molecular manipulations for gene therapy prior to infusion of myeloid cells to patients with neutropenia or genetic disorders of the myeloid system, or to use neutrophils and their bone marrow precursors for infusion to patients with neutropenia or dysfunction of neutrophils.

Preferably said serine protease inhibitors are selected from the group comprising SEQ ID No 2, SEQ ID No 4, SEQ ID No 6, SEQ ID No 8, SEQ ID No 10, SEQ ID No 12, SEQ ID No 14, SEQ ID No 16, SEQ ID No 18 or mixtures thereof.

The invention further provides a method for the prevention of apoptosis of myeloid cells of patients, comprising the administration to said patients in need thereof of a therapeutically effective amount of serine protease inhibitors:

(1) during and after transfection of bone marrow cells performed for gene therapy, (2) during blood stem cell mobilization performed for reconstitution of hematopoiesis and/or (3) during infusion of cells of the myeloid lineage for reconstitution of hematopoiesis for gene therapy or for treatment of neutropenia by infusion of neutrophils.

Preferably said serine protease inhibitors are selected from the group comprising SEQ ID No 2, SEQ ID No 4, SEQ ID No 6, SEQ ID No 8, SEQ ID No 10, SEQ ID No 12, SEQ ID No 14, SEQ ID No 16, SEQ ID No 18 or mixtures thereof.

The invention also provides a kit for the diagnosis, prognosis, prophylaxis or treatment of neutropenia in a mammal, characterized in that said kit comprises serine protease inhibitors, optionally with reagents and/or instructions for use. Preferably said serine protease inhibitors comprise a detectable label or can bind to a detectable label to form a detectable complex. Also preferably said serine protease inhibitors is a Kallikrein inhibitor and preferably said Kallikrein inhibitor is selected amongst hK2, hK3, hK4, hK5, hK6, hK7, hK8, hK9 hK10, hK11, hK12, hK13, hK14, hK15 inhibitors or mixtures thereof. Preferably said serine protease inhibitors are selected from the group comprising SEQ ID No 2, SEQ ID No 4, SEQ ID No 6, SEQ ID No 8, SEQ ID No 10, SEQ ID No 12, SEQ ID No 14, SEQ ID No 16, SEQ ID No 18 or mixtures thereof.

Other objects and advantages will become apparent to those skilled in the art from a review of the ensuing detailed description, which proceeds with reference to the following illustrative drawings, and the attendant claims.

BRIEF DESCRIPTION OF THE FIGURES

FIGS. 1A, 1B, 1C, 1D, 2A and 2B: show Annexin-V staining of neutrophils and T-cells upon incubation with protease inhibitors MDPK67b and MDOKG9.

FIGS. 1A, 1B, 1C and 1D: Annexin-V staining of neutrophils and T-cells upon incubation with MDPK67b. Cells were incubated for 24 or 48 hours with MDPK67b at concentrations ranging from 6 μM to 60 μM, as indicated, or PBS as control. Apoptosis was assessed by Annexin V staining and FACS analysis. Indicated leukocyte populations were gated based on their appearance in a forward scatter/sideward scatter FACS dot plot (neutrophils) or by positive staining for CD3 (T cells).

FIGS. 2A and 2B: Annexin-V staining of neutrophils upon incubation with MDPK67b or MDOKG9 (OKDG9).

Neutrophils were incubated for 18 hours with MDPK67b or MDOKG9 concentrations ranging from 60 μM (dilution 1) to 60 μM (dilution 7) as indicated. Apoptosis was assessed as outlined above.

FIGS. 3A, 3B and 3C: show comparison of various cell culture conditions through Annexin-V staining of MDPK67b treated neutrophils.

Neutrophils were cultured with the indicated concentrations of MDPK67b. PBS without MDPK67b served as a control. Neutrophils were plated (100 μl/well) either at $5 \times 10^6$/ml (high density) or $3 \times 10^5$/ml (low density) and neutrophil apoptosis was assessed by AnnexinV staining and FACS analysis. Culturing of $5 \times 10^6$/ml neutrophils in serum free medium (X-Vivo 15) instead of RPMI10% FCS was assessed in parallel.

FIGS. 4A, 4B, 4C, 4D, 5A, 5B and 5C: show reversion of MDPK67b mediated neutrophil protection by tyrosine kinase inhibitors.

FIGS. 4A, 4B, 4C and 4D: Effect of MDPK67b on CD16 and CD11b levels of cultured neutrophils. Neutrophils were cultured with the indicated concentrations of MDPK67b and percentage of neutrophils expressing high levels of CD16 or CD11b was assessed by FACS. Representative FACS plots are shown.

Figure 4A:
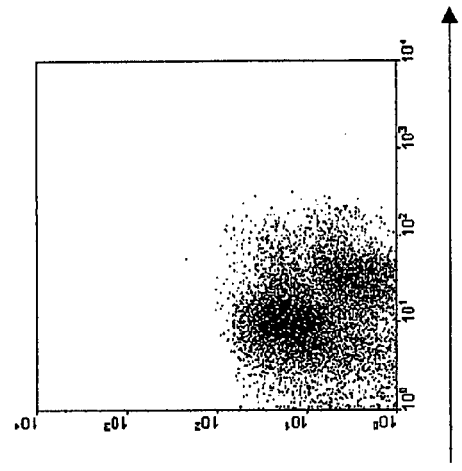
Figure 4C:
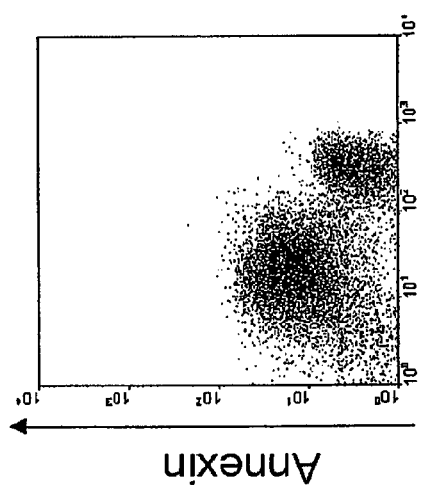
Figure 4B:
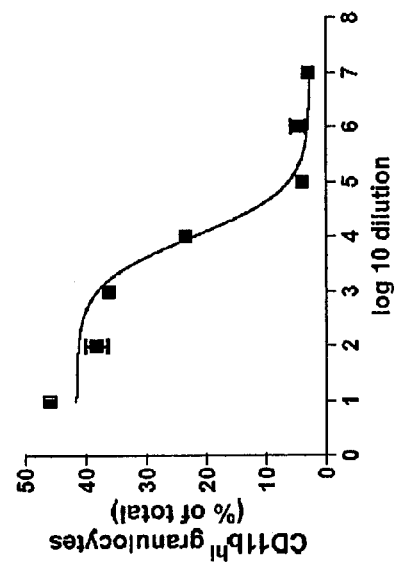
Figure 4D:
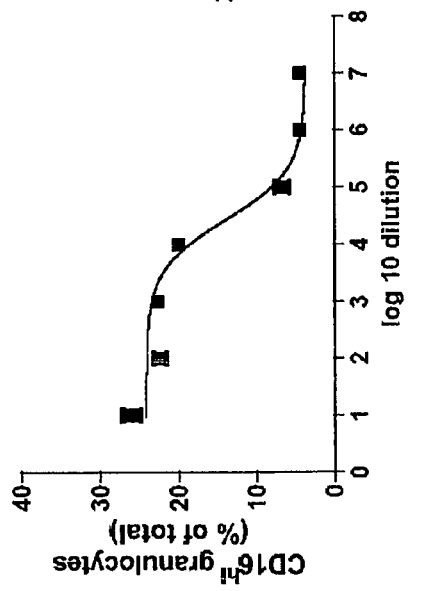
Figure 5A:
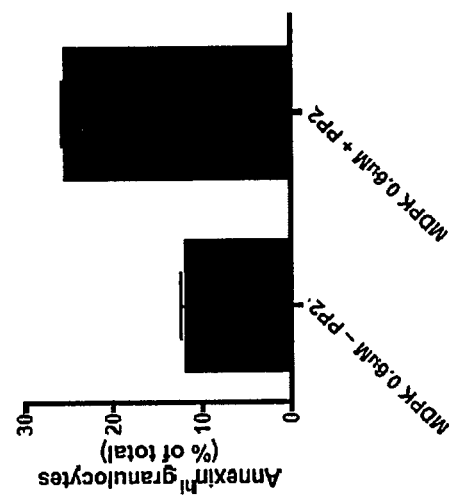
Figure 5B:
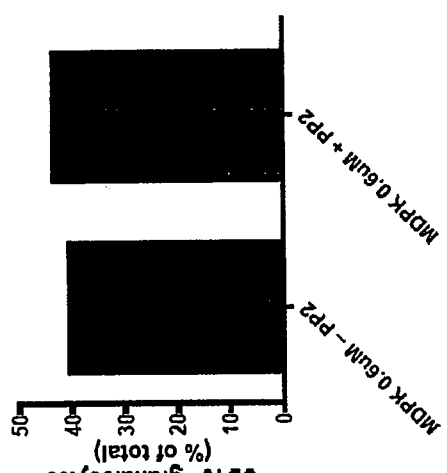
Figure 5C:
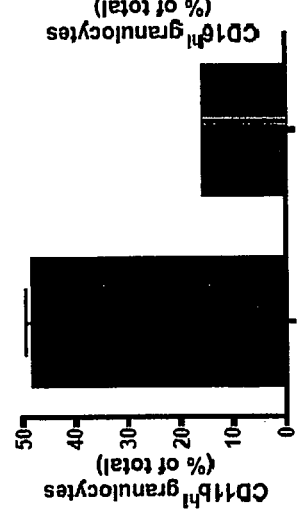

FIGS. 5A, 5B and 5C: Reversion of effect of MDPK67b on CD16 and CD11b neutrophils levels by PP2. Neutrophils were cultured with the indicated concentrations of MDPK67b in presence or absence of the Src tyrosine kinase inhibitor PP2 (final concentration 10 μM). Apoptosis and relative frequencies of CD11b and CD16 high expressing neutrophils were measured by FACS analysis.

Figure 6A:
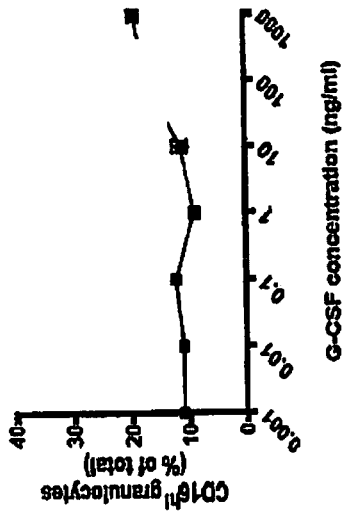
Figure 6B:
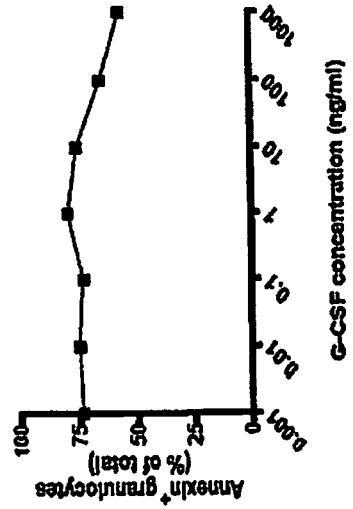
Figure 6C:
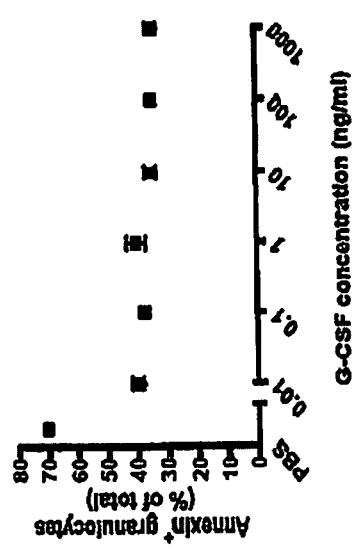

FIGS. 6A, 6B and 6C: show effect of G-CSF on neutrophil in vitro apoptosis.

Neutrophils were cultured with the indicated concentrations of G-CSF and neutrophil Apoptosis (FIG. 6A) and down-regulation of CD 16 expression (FIG. 6B) were analyzed by FACS. FIG. 6C: Neutrophils were cultured with MDPK67b (0.6 μM) and titrated amounts of G-CSF (concentrations as indicated). Neutrophils cultured in medium and PBS (without MDPK67b) served as a control.

Figure 7C:
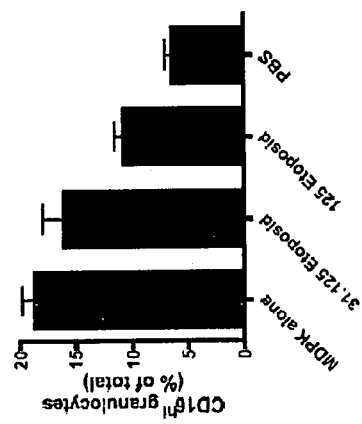
Figure 7A:
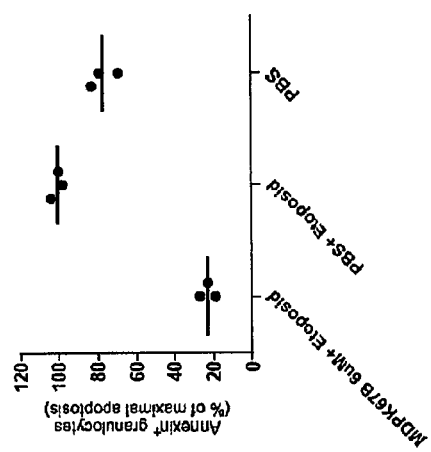
Figure 7B:
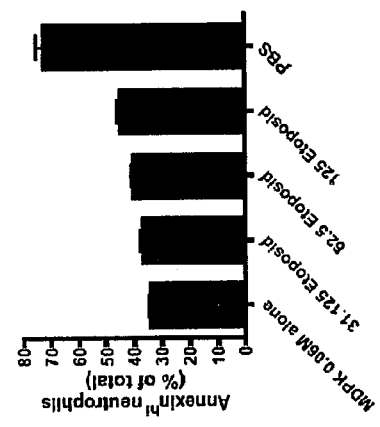

FIGS. 7A, 7B and 7C: show Annexin-V and CD16 staining of neutrophils treated with MDPK67b and Etoposid.

FIG. 7A: Annexin-V staining of neutrophils treated with MDPK67b and Etoposid. Cells were incubated during 18 hours with MDPK67b (6 82 M) plus Etoposid (125 μg/ml), Etoposid alone or PBS. Apoptosis was assessed by Annexin V staining and FACS analysis. Relevant leukocyte populations were gated based on their appearance in a forward scatter or sideward scatter FACS dot plot.

FIG. 7B: Annexin-V staining of neutrophils treated with low MDPK67b and increasing Etoposid concentrations. Cells were incubated for 18 hours with MDPK67b (0.06 μM) alone or MDPK67b (0.06 μM) plus increasing concentrations of Etopsid (in μg/ml) as indicated or PBS. Apoptosis was assessed by Annexin V staining and FACS analysis was performed as mentioned above.

FIG. 7C: CD16 staining of neutrophils treated with MDPK67b and Etoposid. Cells were incubated for 18 hours with MDPK67b (0.06 μM alone or MDPK67b (0.06 μM) plus increasing concentrations of Etopsid (in μg/ml) as indicated or PBS. Percentages of CD16 high expressing neutrophils were assessed by FACS analysis.

DETAILED DESCRIPTION OF THE INVENTION

Some of the serine proteases of the chymotrypsin superfamily, including t-PA, plasmin, u-PA and the proteases of the blood coagulation cascade are large molecules that contain, in addition to the serine protease catalytic domain, other structural domains responsible in part for regulation of their activity (Barrett, 1986; Gerard et al, 1986; Blasi et al., 1986).

Among important serine proteases are trypsin-like enzymes, such as trypsin, tryptase, thrombin, kallikrein, and factor Xa. The serine protease targets are associated with processes such as blood clotting; complement mediated lysis, the immune response, inflammation, pain sensing, glomerulonephritis, pancreatitis, cancer, regulating fertilization, bacterial infection and viral maturation. By inhibiting serine proteases which have high specificity for a particular target, one can inhibit in vivo numerous biological processes, which may have dramatic effects on a host.

Serine proteinase inhibitors (serpins) comprise a diverse group of proteins that form a superfamily already including more than 100 members, from such diverse organisms as viruses, plants and humans. Serpins have evolved over 500 million. years and diverged phylogenetically into proteins with inhibitory function and non-inhibitory function (Hunt and Dayhoff, 1980). Non-inhibitory serpins such as ovalbumin lack protease inhibitory activity (Remold-O'Donnell, 1993). The primary function of serpin family members appears to be the neutralization of overexpressed serine proteinase activity (Potempa et al., 1994). Serpins play a role in extracellular matrix remodeling, modulation of inflammatory response and cell migration (Potempa et al., 1994).

Serine protease inhibitors are divided into the following families: the bovine pancreatic trypsin inhibitor (Kunitz) family, also known as basic protease inhibitor (Ketcham et al., 1978); the Kazal family; the Streptomyces subtilisin inhibitor family; the serpin family; the soybean trypsin inhibitor (Kunitz) family; the potato inhibitor family; and the Bowman-Birk family (Laskowski et al., 1980; Read et al., 1986; Laskowski et. al., 1987). Serine protease inhibitors belonging to the serpin family include the plasminogen activator inhibitors PAI-1, PAI-2 and PAI-3, C1 esterase inhibitor, alpha-2-antiplasmin, contrapsin, alpha-1-antitrypsin, antithrombin III, protease nexin I, alpha-1-antichymotrypsin, protein C inhibitor, heparin cofactor II and growth hormone regulated protein (Carrelletal., 1987; Sommeretal., 1987; Suzuki et al., 1987; Stump et al., 1986).

Many of the serine protease inhibitors have a broad specificity and are able to inhibit both the chymotrypsin superfamily of proteases, including the blood coagulation serine proteases, and the Streptomyces subtilisin superfamily of serine proteases (Laskowski et al., 1980). The inhibition of serine proteases by serpins has been reviewed in Travis et al. (1983); Carrelletal. (1985); and Sprengers et al. (1987). Crystallographic data are available for a number of intact inhibitors including members of the BPTI, Kazal, SSI, soybean trypsin and potato inhibitor families, and for a cleaved form of the serpin alpha-1-antitrypsin (Read et al., 1986). Despite the fact that these serine protease inhibitors are proteins of diverse size and sequence, the intact inhibitors studied to date all have in common a characteristic loop, termed the reactive site loop, extending from the surface of the molecule that contains the recognition sequence for the active site of the cognate serine protease (Levin et al., 1983). The structural similarity of the loops in the different serine protease inhibitors is remarkable (Papamokos et al., 1982). The specificity of each inhibitor is thought to be determined primarily by the identity of the amino acid that is immediately amino-terminal to the site of potential cleavage of the inhibitor by the serine protease. This amino acid, known as the Pi site residue, is thought to form an acyl bond with the serine in the active site of the serine protease (Laskowski et al., 1980). Whether or not a serpin possesses inhibitory function depends strongly on the consensus sequence located in the hinge region of the reactive site loop near the carboxy-terminus of the coding region. Outside of the reactive site loop, the serine protease inhibitors of different families are generally unrelated structurally, although the Kazal family and Streptomyces subtilisin family of inhibitors display some structural and sequence similarity.

As used herein, the following definitions are supplied in order to facilitate the understanding of the present invention.

"A" or "an" means "at least one" or "one or more."

The term "comprise" is generally used in the sense of include, that is to say permitting the presence of one or more features or components.

As used herein, the terms "protein", "polypeptide", "polypeptidic", "peptide" and "peptidic" or "peptidic chain" are used interchangeably herein to designate a series of amino acid residues connected to the other by peptide bonds between the alpha-amino and carboxy groups of adjacent residues.

"Amino acid residue" means any amino acid residue known to those skilled in the art. This encompasses naturally occurring amino acids (including for instance, using the three-letter code, Ala, Arg, Asn, Asp, Cys, Gln, Glu, Gly, His, Ile, Leu, Lys, Met, Phe, Pro, Ser, Thr, Trp, Tyr, Val), as well as rare and/or synthetic amino acids and derivatives thereof (including for instance Aad, Abu, Acp, Ahe, Aib, Apm, Dbu, Des, Dpm, Hyl, McLys, McVal, Nva, and the like.

Said amino acid residue or derivative thereof can be any isomer, especially any chiral isomer, e.g. the L- or D-isoform.

By amino acid derivative, we hereby mean any amino acid derivative as known in the art. For instance, amino acid derivatives include residues derivable from natural amino acids bearing additional side chains, e.g. alkyl side chains, and/or heteroatom substitutions.

"Fragments" refer to sequences sharing at least 40% amino acids in length with the respective sequence of the substrate active site. These sequences can be used as long as they exhibit the same properties as the native sequence from which they derive. Preferably these sequences share more than 70%, preferably more than 80%, even more preferably more than 90%, in particular more than 95% amino acids in length with the respective sequence the substrate active site.

The present invention also includes variants of the substrate active site sequence. The term "variants" refer to polypeptides having amino acid sequences that differ to some extent from a native sequence polypeptide that is amino acid sequences that vary from the native sequence by conservative amino acid substitutions, whereby one or more amino acids are substituted by another with same characteristics and conformational roles. The amino acid sequence variants possess substitutions, deletions, and/or insertions at certain positions within the amino acid sequence of the native amino acid sequence. Conservative amino acid substitutions are herein defined as exchanges within one of the following five groups:

I. Small aliphatic, nonpolar or slightly polar residues: Ala, Ser, Thr, Pro, Gly
II. Polar, positively charged residues: His, Arg, Lys
III. Polar, negatively charged residues: and their amides: Asp, Asn, Glu, Gln
IV. Large, aromatic residues: Phe, Tyr, Trp
V. Large, aliphatic, nonpolar residues: Met, Leu, Ile, Val, Cys.

The term "kallikrein" relates to glandular or tissue kallikreins. Glandular or tissue kallikreins are a sub-family of serine proteases, with a high degree of substrate specificity and diverse expression in various tissues and biological fluids. The term "kallikrein" appeared in the literature for the first time in the 1930s, when large amounts of protease enzymes were found in pancreas isolates (pancreas is "Kallikreas" in Greek) (Kraut et al. 1930, Werle 1934). Nowadays kallikrein enzymes are divided into two groups, plasma and tissue kallikreins, which differ significantly in their molecular weight, substrate specificity, immunological characteristics, gene structure, and type of the kinin released.

Kallikreins comprise a family of 15 homologous single chain, secreted serine endopeptidases of ~25-30 kDa, with orthologues present in species from at least six mammalian orders. These kallikreins are hK2, hK3, hK4, hK5, hK6, hK7, hK8, hK9 hK10, hK11, hK12, hK13, hK14 and hK15. Preferably kallikreins are hK2, hK4, hK11 and hK14.

"Antibody", as used herein, refers to a class of plasmaproteins produced by the B-cells of the immune system after stimulation by an antigen. Mammal (i.e. Human) antibodies are immunoglobulins of the Ig G, M, A, E or D class. The term "antibody" as used for the purposes of this invention includes, but is not limited to, polyclonal, monoclonal, chimeric, humanized, human, internalizing, neutralizing, anti-idiotypic antibodies, immunologically-active fragments or derivatives thereof, recombinant proteins having immunologically-activity, and immunoconjugates which bind a kallikrein or a membrane anchored serine protease.

The terms "cancer" and "cancerous" refer to or describe the physiological condition in mammals that is typically characterized by unregulated cell growth.

"Disease", as used herein, refers to a pathological condition of a part, organ, or system of an organism resulting from various causes, such as infection, genetic defect, or environmental stress, and characterized by an identifiable group of signs or symptoms.

"Mammal" for purposes of treatment refers to any animal classified as a mammal, including humans, domestic and farm animals, and zoo, sports, or pet animals, such as dogs, horses, cats, cows, monkeys etc. Preferably, the mammal is human.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder.

The term "subject" refers to patients of human or other mammal and includes any individual it is desired to examine or treat using the methods according to the present invention. However, it will be understood that "patient" does not automatically imply that symptoms or diseases are present.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, the term "protease" refers to a class of enzymes which recognizes a molecule and cleaves an activation sequence in the molecule. The protease can be an endopeptidase which cleaves internal peptide bonds. Alternatively, the protease can be an exopeptidase which hydrolyzes the peptide bonds from the N-terminal end or the C-terminal end of the polypeptide or protein molecule. The protease folds into a conformation to form a catalytic site which receives and cleaves the activation sequence.

"Inhibitors" refer to a polypeptide, or a chemical compound, that specifically inhibit the function of a kallikrein or serine protease by, preferably, binding to said kallikrein or serine protease.

"Reactive Serpin Loop" or "Reactive Site Loop" or RSL refers to an exposed flexible reactive-site loop found in serpin and which is implicated in the interaction with the putative target protease. From the residue on the amino acid side of the scissile bond, and moving away from the bond, residues are conventionally called P1, P2, P3, etc. Residues that follow the scissile bond are called P1', P2', P3', etc. Usually, the RSL is composed of 6 to 12 amino acid residues.

"Serine protease" or serpin according to the invention can be selected from the group comprising the α-1antichymotrypsin (ACT), protein C inhibitor (PCI), α-1antiproteinase (AAT), human α-1antitrypsin-related protein precursor (ATR), α-2-plasmin inhibitor (AAP), human anti-thrombin-III precursor (ATIII), protease inhibitor 10 (PI10), human collagen-binding protein 2 precursor (CBP2), protease inhibitor 7 (PI7), protease inhibitor leuserpin 2 (HLS2), human plasma protease C1 inhibitor (C1 INH), monocyte/neutrophil elastase inhibitor (M/NEI), plasminogen activator inhibitor-3 (PAI3), protease inhibitor 4 (PI4), protease inhibitor 5 (PI5), protease inhibitor 12 (PI12), human plasminogen activator inhibitor-1 precursor endothelial (PAI-1), human plasminogen activator inhibitor-2 placental (PAI2), human pigment epithelium-derived factor precursor (PEDF), protease inhibitor 6 (PI6), protease inhibitor 8 (PI8), protease inhibitor 9 (PI9), human squamous cell carcinoma antigen 1 (SCCA-1), human squamous cell carcinoma antigen 2 (SCCA-2), T4-binding globulin (TBG), Megsin, and protease inhibitor 14 (PI14), fragments thereof, molecular chimeras thereof, combinations thereof and/or variants thereof.

Since most of these serpins have different names, Applicant includes below a table summarizing their specifications:

TABLE I

| Serpin | Accession Number | SEQ ID Number | RSL sequence |
|---|---|---|---|
| PI or AAT, A1AT_HUMAN ALPHA-1-ANTITRYPSIN PRECURSOR (ALPHA-1 PROTEASE INHIBITOR) (ALPHA-1-ANTIPROTEINASE) | sp\|P01009\| | SEQ ID No 19 | GTEAAGAMFLEAIPMSIPPE |
| PIL or ATR, A1AU_HUMAN ALPHA-1-ANTITRYPSIN-RELATED PROTEIN PRECURSOR | sp\|P20848\| | SEQ ID No 20 | GTEATGAPHLEEKAWSKYQT |
| PLI OR AAP, A2AP_HUMAN ALPHA-2-ANTIPLASMIN PRECURSOR (ALPHA-2-PLASMIN INHIBITOR) (ALPHA-2-PI) (ALPHA-2-AP) | sp\|P08697\| | SEQ ID No 21 | GVEAAAATSIAMSRMSLSSF |
| AACT, AACT_HUMAN ALPHA-1-ANTICHYMOTRYPSIN PRECURSOR (ACT) | sp\|P01011\| | SEQ ID No 22 | GTEASAATAVKITLLSALVE |
| AT3, ANT3_HUMAN ANTITHROMBIN-III PRECURSOR (ATIII) | sp\|P01008\| | SEQ ID No 23 | GSEAAASTAVVIAGRSLNPN |
| PI10, BOMA_HUMAN BOMAPIN (PROTEASE INHIBITOR 10) | sp\|P48595\| | SEQ ID No 24 | GTEAAGSGSEIDIRIRVPS |
| CBP2, CBP2_HUMAN COLLAGEN-BINDING PROTEIN 2 PRECURSOR (COLLIGIN 2) | sp\|P50454\| | SEQ ID No 25 | GNPFDQDIYGREELRSPKLF |
| PI7 or PN1, GDN_HUMAN GLIA DERIVED NEXIN PRECURSOR (GDN) (PROTEASE NEXIN I) (PN-1) (PROTEASE INHIBITOR 7) | sp\|P07093\| | SEQ ID No 26 | GTKASAATTAILIARSSPPW |
| HCF2, HEP2_HUMAN HEPARIN COFACTOR II PRECURSOR (HC-II) (PROTEASE INHIBITOR LEUSERPIN 2) (HLS2) | sp\|P05546\| | SEQ ID No 27 | GTQATTVTTVGFMPLSTQVR |
| C1NH or C1IN, IC1_HUMAN PLASMA PROTEASE C1 INHIBITOR PRECURSOR (C1 INH) | sp\|P05155\| | SEQ ID No 28 | GVEAAAASAISVARTLLVFE |

TABLE I-continued

| Serpin | Accession Number | SEQ ID Number | RSL sequence |
|---|---|---|---|
| ELANH2 or PI2, ILEU_HUMAN LEUKOCYTE ELASTASE INHIBITOR (LEI) (MONOCYTE/NEUTROPHIL ELASTASE INHIBITOR) (M/NEI) (EI) | sp\|P30740\| | SEQ ID No 29 | GTEAAAATAGIATFCMLMPE |
| PCI or PLANH3 or PROCI, IPSP_HUMAN PLASMA SERINE PROTEASE INHIBITOR PRECURSOR (PCI) (PROTEIN C INHIBITOR) (PLASMINOGEN ACTIVATOR INHIBITOR-3) (PAI3) | sp\|P05154\| | SEQ ID No 30 | GTRAAAATGTIFTFRSARLN |
| PI4 or KST, KAIN_HUMAN KALLISTATIN PRECURSOR (KALLIKREIN INHIBITOR) (PROTEASE INHIBITOR 4) | sp\|P29622\| | SEQ ID No 31 | GTEAAAATTFAIKFFSAQTN |
| PI5, MASP_HUMAN MASPIN PRECURSOR (PROTEASE INHIBITOR 5) | sp\|P36952\| | SEQ ID No 32 | GGDSIEVPGARILQHKDELN |
| PI12, NEUS_HUMAN NEUROSERPIN PRECURSOR (PROTEASE INHIBITOR 12) | sp\|Q99574\| | SEQ ID No 33 | GSEAAAVSGMIAISRMAVLY |
| PAI1 or PLANH1, sp\|P05121\|PAI1_HUMAN PLASMINOGEN ACTIVATOR INHIBITOR-1 PRECURSOR, ENDOTHELIAL (PAI-1) | sp\|P05121\| | SEQ ID No 34 | GTVASSSTAVIVSARMAPEE |
| PAI2 or PLANH2, PAI2_HUMAN PLASMINOGEN ACTIVATOR INHIBITOR-2, PLACENTAL (PAI-2) (MONOCYTE ARG-SERPIN) (UROKINASE INHIBITOR) | sp\|P05120\| | SEQ ID No 35 | GTEAAAGTGGVMTGRTGHGG |
| PEDF, PEDF_HUMAN PIGMENT EPITHELIUM-DERIVED FACTOR PRECURSOR (PEDF) (EPC-1) | sp\|P36955\| | SEQ ID No 36 | GAGTTPSPGLQPAHLTFPLD |
| PI6 or PTI, PTI6_HUMAN PLACENTAL THROMBIN INHIBITOR (CYTOPLASMIC ANTIPROTEINASE) (CAP) (PROTEASE INHIBITOR 6) | sp\|P35237\| | SEQ ID No 37 | GTEAAAATAAIMMMRCARFV |
| PI8, PTI8_HUMAN CYTOPLASMIC ANTIPROTEINASE 2 (CAP2) (CAP-2) (PROTEASE INHIBITOR 8) | sp\|P50452\| | SEQ ID No 38 | GTEAAAATAVVRNSRCSRME |
| PI9, PTI9_HUMAN CYTOPLASMIC ANTIPROTEINASE 3 (CAP3) (CAP-3) (PROTEASE INHIBITOR 9) | sp\|P50453\| | SEQ ID No 39 | GTEAAAASSCFVVAECCMES |
| SCCA1, SCC1_HUMAN SQUAMOUS CELL CARCINOMA ANTIGEN 1 (SCCA-1) (PROTEIN T4-A) | sp\|P29508\| | SEQ ID No 40 | GAEAAAATAVVGFGSSPAST |
| SCCA2, SCC2_HUMAN SQUAMOUS CELL CARCINOMA ANTIGEN 2 (SCCA-2) (LEUPIN) | sp\|P48594\| | SEQ ID No 41 | GVEAAAATAVVVVELSSPST |
| TBG, THBG_HUMAN THYROXINE-BINDING GLOBULIN PRECURSOR (T4-BINDING GLOBULIN) | sp\|P05543\| | SEQ ID No 42 | GTEAAAVPEVELSDQPENTF |
| MEGSIN | gi\|4505149\|ref\|NP_003775.1\| | SEQ ID No 43 | GTEATAATGSNIVEKQLPQS |
| PI14, pancpin, TSA2004 | gi\|3724282\|dbj\|BAA33766.1\| | SEQ ID No 44 | GSEAATSTGIHIPVIMSLAQ |

Advantageously, the serine protease inhibitor of the invention may be a serine protease trypsin-like enzyme and preferably a Kallikrein inhibitor. Kallikrein inhibitors of the invention are selected amongst hK2, hK3, hK4, hK5, hK6, hK7, hK8, hK9 hK10, hK11, hK12, hK13, hK14 or hK15 inhibitors. Preferably kallikreins inhibitors are selected among hK2, hK4, hK11, hK5 and hK14 inhibitors. More preferably, the kallikrein inhibitor is an hK2 inhibitor.

Encompassed by the present invention are recombinant inhibitor proteins of a Kallikrein, comprising a serpin sequence wherein the Reactive Serpin Loop P6-P6' of said serpin sequence comprises at least one substrate active site sequence specific for said Kallikrein, biologically active fragments thereof, a molecular chimera thereof, a combination thereof and/or variants thereof. Said at least one substrate active site sequence specific for said Kallikrein is a substrate peptide selected by Kallikrein using a phage-displayed random pentapeptide library as disclosed in International Patent Application PCT/IB2004/001040 (University of Lausanne).

In particular, in case the kallikrein inhibitor is an inhibitor directed against hK2, said inhibitor can be selected among those disclosed in International Patent Application PCT/IB2004/001040, which content is incorporated herein by reference in its entirety. Preferably, the kallikrein inhibitor of the invention may be selected from the group comprising MD820, MD62, MD61, MD67 and MDCI. Most preferably this inhibitor is MD62 or MD61 and even more preferably the inhibitor is MDPK67b. This application discloses a chimeric inhibitor protein of a protease comprising an inhibiting polypeptidic sequence and at least one polypeptidic sequence of a substrate-enzyme interaction site specific for a protease as well as a method for producing the chimeric inhibitor protein of a protease. Preferably, the purified and isolated DNA sequence encoding the serine protease inhibitor of the invention is selected from the group comprising SEQ ID No 1, SEQ ID No 3, SEQ ID No 5, SEQ ID No 7, SEQ ID No 9, SEQ ID No 11, SEQ ID No 13 and SEQ ID No 15. The most preferably, the purified and isolated DNA sequence encoding the serine protease inhibitor of the invention is SEQ ID No 15.

As an example of serine protease inhibitor according to the invention, Applicants have surprisingly found 6 new chimeric inhibitor proteins specific for the protease hK2 as resumed below in table II, these inhibitors are:

TABLE II

| Chimeric inhibitors | Other name | SEQ ID No (protein) |
|---|---|---|
| rACT$_{8.20}$ | MD820 | 2 |
| rACT$_{6.2}$ | MD62 | 4 |
| rACT$_{8.3}$ | MD83 | 6 |
| rACT$_{6.7}$ | MD67 | 8 |
| rACT$_{6.1}$ | MD61 | 10 |
| ACT$_{5.18}$ | MD518 | 12 |
| MDCI | | 14 |
| MDPK67b | | 16 |

These chimeric inhibitor proteins have been obtained by modifying the RSL of α1-antichymotrypsin (rACT), which is known to inhibit a large panel of human enzymes such as chymotrypsin, mast cell chymase, cathepsin G, prostatic kallikreins hK2 and PSA (hK3), in order to change the specificity of this serpin. Peptide sequences, selected as substrates for the enzyme hK2 by phage display technology as explained in International Patent Application PCT/IB2004/001040, have been used to replace the scissile bond and neighbor amino acid residues of the RSL. Recombinant inhibitors were produced in bacteria and purified by affinity chromatography.

Additionally, applicants have also found that replacing residues P3-P3' located in RSL structure of rACTWT by substrate pentapeptide coding for the RSL of Protein C inhibitor (PCI) lead to the production of a chimeric inhibitor (MDCI) which is able to inhibit kallikreins hK2 and hK3.

In case the kallikrein inhibitor is an inhibitor directed against hK14, then said inhibitor can be selected among those disclosed in the priority International Patent Application PCT/IB2005/000504, which content is incorporated herein by reference in its entirety. Preferably, said recombinant inhibitor may be selected from the group comprising AATG1, AATG1G, AATC11, AATC11G, AATE5, AATE8, AATF11, AATF3, AATG9, ACTG1, AcTG1G, ACTC11, ACTC11G, ACTE5, ACTE8, ACTF11, ACTF3, ACTG9 (SEQ ID No 17), ACTG1V, and ACTC11D. Preferably, said inhibitor protein of an hK14 protease is AATG1, AATG1G, AATC11, AATC11G, AATE5, AATE8, AATF3, AATG9, ACTG1G, ACTC11, ACTC11G, ACTE5, ACTE8, AGTF11, ACTF3, ACTG9 (SEQ ID No 18), ACTG1V, or ACTC11D. This application discloses a chimeric inhibitor protein of an hK14 protease having an inhibiting polypeptidic sequence and at least a polypeptidic sequence of a substrate-enzyme interaction site specific for said hK14 protease, wherein said chimeric inhibitor protein of an hK14 protease has, under physiological conditions, (i) a stoechiometry of inhibition (SI) equal or below to 11.7 after at least 4 hours of incubation, (ii) an association rate (Ka) of at least 7'500 M-1 s-1, (iii) an inhibitory activity of 100% after at least 30 minutes of incubation.

In addition, the inhibiting polypeptidic sequence of the protease inhibitor may also be selected from a cysteine protease since there are now a number of well-documented instances of inhibition of cysteine proteases by serpins (Gettins P. G. W., 2002 "Serpin structure, mechanism, and function" in Chem. Rev, 102, 4751-4803). These examples include inhibition of cathepsins K, L and S by the serpin squamous cell carcinoma antigen1, inhibition of prohormone thiol proteinase by the α-1antichymotrypsin, and inhibition of members of the caspase family, icluding caspase 1 (interleukine 1β converting enzyme), caspase 3, and caspase 8 by the viral serpin crmA and caspases 1, 4 and 8 by the human serpin PI9.

Also contemplated by the present invention are mixtures of serine protease inhibitors, antibodies, Peptabodies and biologically active fragments thereof.

Antibodies according to the invention can bind selectively a kallikrein or a serine protease and will not bind (or will bind weakly) to a non-target polypeptide. They can also bind to a naturally occurring kallikrein or serine protease or to recombinants polypeptide thereof. The antibodies of the invention can bind a kallikrein or serine protease expressed by a cell i.e. expressed by a cell includes cell-surface, membrane-bound, cytoplasmic or secreted forms. They can also bind one or more domains on the kallikrein or the serine protease, including the cytoplasmic, transmembrane, and/or extracellular domain(s). Alternatively, they can bind to any of the kallikrein or serine protease in their native and/or denatured forms.

It is understood by those skilled in the art that the regions or epitopes of the kallikrein or serine protease to which an antibody is directed can vary with the intended application.

The antibody according to the invention can recognize and bind any portion of the kallikrein or the serine protease, including the cytoplasmic domain, transmembrane domain, and/or the extracellular domain, or any portion thereof such as fragments or derivatives thereof.

Antibodies according to the invention can be polyclonal preparations which include a population of different antibodies directed against a different epitope on the immunogen, such as a kallikrein or serine protease used as an immunogen.

Polyclonal antibodies can be produced by methods well-known in the art. In general, any antibody (e.g., monoclonal, polyclonal, and the like) can be raised using an isolated kallikrein or a serine protease, or a fragment as the immunogen. In addition, the immunogen can be a fusion protein including all or a portion of the target polypeptides fused to V5, His, maltose-binding protein, GST, or human Ig. For example, polyclonal antibodies have been previously raised using a fusion protein having the extracellular domain of, for example, human hepsin fused to maltose-binding protein (Y Kazama, et al., 1995 J Biol Chem 270:66-72).

The antibodies according to the invention can be monoclonal antibodies that bind a specific antigenic site present on the kallikrein or the serine protease.

Methods for preparing an immunogen and immunizing an animal are well-known in the art (Kohler and Milstein 1975 Nature 256:495-497; Brown et al. 1981 J Immunol 127:539-46; Brown et al., 1980 J Biol Chem 255:4980-83; Yeh et al., 1976 Proc Natl Acad Sci USA 76:2927-31; Yeh et al., 1982 Int J Cancer 29:269-75; Kozbor et al., 1983 Immunol Today 4:72; Cole et al., 1985 Monoclonal Antibodies and Cancer Therapy, Alan R. Liss, Inc., pp. 77-96; U.S. Pat. No. 4,816,567; Clackson, et al., 1991 Nature 352:624-628; Marks, et al., 1991 J Mol Biol 222:581-597).

The present invention also envisioned the case where the Kallikrein inhibitors and/or the serine protease inhibitors are in the form of Peptabodies. A "Peptabody" as disclosed in WO 98/18943 (Kajava et al.) and WO2004087766 (Université de Lausanne) which are incorporated herein by reference in their entirety, is a high avidity molecule which uses the multimerization concept for inducing aberrant cell signals. The multimerization domain consists of a part of human cartilage oligomeric matrix protein (COMP), which is fused to a hinge region or spacer (preferably containing 19 amino acids from human IgA) and a domain (binding domain) capable of binding to an acceptor (ligand). The concept of peptabody molecule allows a tight binding on cells or tissues expressing high level of Kallikrein marker and serine protease. "Decabodies" are constructed on the same principle with the difference that they possess ten arms and consequently ten binding domains.

Usually, the diseases according to the invention are diseases in which the number of polymorphonuclear leukocytes, the neutrophils have become a problem by being decreased due to infections, septicemia, irradiation, chemotherapy, side effects of drugs or the action of toxic chemicals.

The invention also includes topical application of kallikrein inhibitors in diabetic skin ulcers to prevent cell death of neutrophils and thereby restore cellularity and functions of neutrophils.

The invention also includes the in-vitro use of kallikrein inhibitors or the serine protease inhibitors for preparation of neutrophils and their bone marrow precursors to perform molecular manipulations for gene therapy or to use neutrophils and their bone marrow precursors for infusions to patients.

The invention includes the treatment of patients receiving stem cells or myeloid precursor cells or neutrophil transfusions with kallikrein inhibitors or the serine protease inhibitors.

The present invention is also directed to a pharmaceutical composition comprising the kallikrein inhibitor and/or the serine protease inhibitor as described herein as an active agent, optionally in combination with one or more pharmaceutically acceptable carriers.

Preferably the composition, as a pharmaceutical composition, according to the invention is to be administered to a patient in need of treatment via any suitable route, usually orally or by injection into the bloodstream or CSF, or subcutaneously or directly into the site of interest, or close to this site.

Preferably, the composition according to the invention may also be added to infusion solutions prepared for infusions of bone marrow cells, myeloid cells and neutrophils.

According to another embodiment, the composition of the invention may also be added to solutions which are used in in-vitro manipulations of bone marrow cells and neutrophils for gene therapy or in cell freezing for storing of the cells.

According to a further embodiment, the composition of the invention may be applied locally to the skin in diabetic or ischemic skin ulcers.

The precise dose will depend upon a number of factors, including whether the composition is for prophylaxis or for treatment, the precise nature of the composition, and the nature of the detectable or functional label attached to the Kallikrein inhibitor or the serine protease inhibitor.

The present pharmaceutical composition comprises as an active substance a pharmaceutically effective amount of the composition as described, optionally in combination with pharmaceutically acceptable carriers, diluents and adjuvants.

"A pharmaceutically effective amount" refers to a chemical material or compound which, when administered to a human or animal organism induces a detectable pharmacological and/or physiologic effect.

The pharmaceutically effective amount of a dosage unit of the kallikrein inhibitor and/or the serine protease inhibitor as described herein usually is in the range of 0.001 ng to 100 µg per kg of body weight of the patient to be treated.

The pharmaceutical composition may contain one or more pharmaceutically acceptable carriers, diluents and adjuvants.

Acceptable carriers, diluents and adjuvants which facilitates processing of the active compounds into preparation which can be used pharmaceutically are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN®, PLURONICS® or polyethylene glycol (PEG).

The form of administration of the pharmaceutical composition may be systemic or topical. For example, administration of such a composition may be various parenteral routes such as subcutaneous, intravenous, intradermal, intramuscular, intraperitoneal, intranasal, transdermal, buccal routes or via an implanted device, and may also be delivered by peristaltic means.

The pharmaceutical composition, as described herein, may also be incorporated or impregnated into a bioabsorbable matrix, with the matrix being administered in the form of a suspension of matrix, a gel or a solid support. In addition the matrix may be comprised of a biopolymer.

Sustained-release preparations may be prepared. Suitable examples of sustained-release preparations include semi permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and [gamma] ethyl-L-glutamate, non-degradable ethylene-vinyl acetate, degradable lactic acid-glycolic acid copolymers such as the LUPRON DEPOT(TM) (injectable microspheres composed of lactic acid-glycolic acid copolymer and leuprolide acetate), and poly-D-(-)-3-hydroxybutyric acid.

The formulations to be used for in vivo administration must be sterile. This is readily accomplished for example by filtration through sterile filtration membranes.

It is understood that the suitable dosage of the present composition will be dependent upon the age, sex, health, and weight of the recipient, kind of concurrent treatment, if any and the nature of the effect desired. The appropriate dosage form will depend on the disease, the inhibitor, and the mode of administration; possibilities include tablets, capsules, lozenges, dental pastes, suppositories, inhalants, solutions, ointments and parenteral depots.

Since amino acid modifications of the amino acids (of the inhibitor for example) are also encompassed in the present invention, this may be useful for cross-linking the inhibitor to a water-insoluble matrix or the other macromolecular carriers, or to improve the solubility, adsorption, and permeability across the blood brain barrier. Such modifications are well known in the art and may alternatively eliminate or attenuate any possible undesirable side effect of the peptide and the like.

Usually, the Kallikrein inhibitors or the serine protease inhibitors of the invention can comprise a detectable label or can bind to a detectable label to form a detectable complex.

"Detectable labels" are detectable molecules or detection moiety for diagnostic purposes, such as enzymes or peptides having a particular binding property, e.g. streptavidin or horseradish peroxidase. Detection moiety further includes chemical moieties such as biotin which may be detected via binding to a specific cognate detectable moiety, e. g. labelled avidin.

Preferably, detectable labels include fluorescent labels and labels used conventionally in the art for MRI-CT imagine. A number of fluorescent materials are known and can be utilized as labels. These include, for example, fluorescein, rhodamine, auramine, Texas Red, AMCA blue and Lucifer Yellow.

The Kallikrein inhibitors or the serine protease inhibitors of the invention may carry a radioactive label as the detection moiety, such as the isotopes 3H, 14C, 32P, 35S, 36C1, 51Cr, 57Co, 58Co, 59Fe, 90Y, 121I, 124I, 125I, 131I, 111In, 211At, 198Au, 67Cu, 225Ac, 213bu, 99Tc and 186Re. When radioactive labels are used, known currently available counting procedures may be utilized to identify and quantitate the specific binding members.

In the instance where the label is an enzyme, detection may be accomplished by any of the presently utilized colorimetric, spectrophotometric, fluorospectrophotometric, amperometric or gasometric techniques known in the art.

In the instance of in vivo imaging, the labels of the present invention may be conjugated to an imaging agent rather than a radioisotope(s), including but not limited to a magnetic resonance image enhancing agent. Examples of chelating groups include EDTA, porphyrins, polyamines crown ethers and polyoximes.

Examples of paramagnetic ions include gadolinium, iron, manganese, rhenium, europium, lanthanium, holmium and erbium.

Another subject matter of the present invention is to provide a kit for the diagnosis, prognosis, prophylaxis or treatment of neutropenia in a mammal, said kit comprising the composition of the invention, optionally with reagents and/or instructions for use.

The kit of the present invention may further comprise a separate pharmaceutical dosage form comprising for example an anti-cancer agent selected from the group consisting of chemotherapeutic agents, anti-epidermal growth factor receptors antibodies, radioimmunotherapeutic agents, and combinations thereof.

Generally, the Kit comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The label or package insert indicates that the composition is used for treating the condition of choice, such as netropenia.

Alternatively, or additionally, the Kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The present invention also discloses the use of the composition of the invention, as a pharmacological tool in the development and standardization of in vitro and in vivo test systems for the diagnosis, prognosis, prophylaxis or treatment of neutropenia in mammals.

Also encompassed by the present invention is a detection assay for the diagnosis, prognosis, prophylaxis or treatment of neutropenia in a tissue sample comprising contacting the tissue sample with the composition of the invention, determining and measuring the amount of detected label and correlating this amount to the presence or absence of neutropenia in said tissue sample.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

MDPK67B In Vitro Effect on Neutrophil Cell Survival.

To assess viability of neutrophils in-vitro, peripheral blood from healthy donors was erythrocyte-lyzed and neutrophils or peripheral blood mononuclear cells (PBMCs) were isolated. Cultures in RPMI10%FCS were performed in 96 well microtiter plates ($5\times10^5$cells/well) unless otherwise stated. The percentage of apoptotic neutrophils or PBMCs was assessed based on binding of fluorescent Annexin V-protein binding or measuring of CD11b or CD16 surface expression by FACS (fluorescent activated cell sorter) analysis.

Example 1

MDPK67b Reduced Apoptosis of Neutrophils in Vitro in a Dose-dependent Manner but has No Significant Effect on T-cell Survival FIGS. 1A, 1B, 1C, 1D, 2A and 2B: Annexin-V staining of neutrophils and T-cells upon incubation with protease inhibitors MDPK67b and MDOKG9.

FIGS. 1A, 1B, 1C and 1D: Annexin-V staining of neutrophils and T-cells upon incubation with MDPK67b.

Cells were incubated for 24 or 48 hours with MDPK67b at concentrations ranging from 6 µM to 60 µM, as indicated, or PBS as control. Apoptosis was assessed by Annexin V staining and FACS analysis. Indicated leukocyte populations were gated based on their appearance in a forward scatter/sideward scatter FACS dot plot (neutrophils) or by positive staining for CD3 (T cells).

FIGS. 2A and 2B: Annexin-V staining of neutrophils upon incubation with MDPK67b or MDOKG9 (OKDG9).

Neutrophils were incubated for 18 hours with MDPK67b or MDOKG9 concentrations ranging from 60 µM (dilution 1) to 60 µM (dilution 7) as indicated. Apoptosis was assessed as outlined above.

Conclusion: MDPK67b at doses ranging from 60 µM down to 0.6 µM inhibit apoptosis of neutrophils. MDOKG9 had a similar effect protecting neutrophils entering apoptosis. This effect was specific to neutrophils and MDPK67B did not inhibit apoptosis of monocytes or lymphocytes.

Example 2

MDPK67b Mediated Protection of Neutrophils Against Apoptosis is Independent from Culture Conditions FIGS. 3A, 3B and 3C: Comparison of various cell culture conditions through Annexin-V staining of MDPK67b treated neutrophils.

Neutrophils were cultured with the indicated concentrations of MDPK67b. PBS without MDPK67b served as a control. Neutrophils were plated (100 µl/well) either at 5×10$^6$/ml (high density) or 3×10$^5$/ml (low density) and neutrophil apoptosis was assessed by AnnexinV staining and FACS analysis. Culturing of 5×10$^6$/ml neutrophils in serum free medium (X-Vivo 15) instead of RPMI10% FCS was assessed in parallel.

Conclusion: MDPK67b inhibits apoptosis of neutrophils in vitro independently of cell density and presence or absence of serum in the growth medium.

Example 3

The Src Tyrosine Kinase Inhibitor PP2 Reverses MDPK67b Mediated Decrease in Apoptosis of Neutrophils FIGS. 4A, 4B, 4C, 4D, 5A, 5B and 5C: Reversion of MDPK67b mediated neutrophil protection by tyrosine kinase inhibitors.

FIGS. 4A, 4B, 4C and 4D: Effect of MDPK67b on CD16 and CD11b levels of cultured neutrophils.

Neutrophils were cultured with the indicated concentrations of MDPK67b and percentage of neutrophils expressing high levels of CD16 or CD11b was assessed by FACS. Representative FACS plots are shown.

FIGS. 5A, 5B and 5C: Reversion of effect of MDPK67b on CD16 and CD11b neutrophils levels by PP2.

Neutrophils were cultured with the indicated concentrations of MDPK67b in presence or absence of the Src tyrosine kinase inhibitor PP2 (final concentration 10 µM). Apoptosis and relative frequencies of CD11b and CD16 high expressing neutrophils were measured by FACS analysis.

Conclusion: MDPK67b increases dose-dependently the frequency of neutrophils that express CD16 and CD11b at high levels which is associated with decreased apoptosis. The increased frequency of CD11b high expressing neutrophils and the decreased apoptosis in the presence of MDPK67b can be reversed in the presence of the Src tyrosine kinase inhibitor PP2. Similar effects were observed with orther kinase inhibitors blocking intracellular signaling pathways including the PI3K inhibitor Ly294002 and the ERK inhibitor PD98059.

Example 4

Superior Effect of MDPK67b Compared to G-CSF in Protection of Neutrophils from Apoptosis FIGS. 6A, 6B and 6C: Effect of G-CSF on neutrophil in vitro apoptosis.

Neutrophils were cultured with the indicated concentrations of G-CSF and neutrophil Apoptosis (FIG. 6A) and down-regulation of CD 16 expression (FIG. 6B) were analyzed by FACS. FIG. 6C: Neutrophils were cultured with MDPK67b (0.6 µM) and titrated amounts of G-CSF (concentrations as indicated). Neutrophils cultured in medium and PBS (without MDPK67b) served as a control.

Conclusion: The effect of MDPK67b on neutrophil apoptosis is not affected by G-CSF which alone has only a mild protecting effect on neutrophil apoptosis.

Example 5

MDPK67b Reduces Cytostatic Drug-induced Apoptosis of Neutrophils

FIGS. 7A, 7B and 7C: Annexin-V and CD16 staining of neutrophils treated with MDPK67b and Etoposid.

FIG. 7A: Annexin-V staining of neutrophils treated with MDPK67b and Etoposid.

Cells were incubated during 18 hours with MDPK67b (6 µM) plus Etoposid (125 µg/ml), Etoposid alone or PBS. Apoptosis was assessed by Annexin V staining and FACS analysis. Relevant leukocyte populations were gated based on their appearance in a forward scatter or sideward scatter FACS dot plot.

FIG. 7B: Annexin-V staining of neutrophils treated with low MDPK67b and increasing Etoposid concentrations.

Cells were incubated for 18 hours with MDPK67b (0.06 µM) alone or MDPK67b (0.06 µM) plus increasing concentrations of Etopsid (in µg/ml) as indicated or PBS. Apoptosis was assessed by Annexin V staining and FACS analysis was performed as mentioned above.

FIG. 7C: CD16 staining of neutrophils treated with MDPK67b and Etoposid Cells were incubated for 18 hours with MDPK67b (0.06 µM alone or MDPK67b (0.06 µM) plus increasing concentrations of Etopsid (in µg/ml) as indicated or PBS. Percentages of CD16 high expressing neutrophils were assessed by FACS analysis.

Conclusion: Even high doses (up to 125 µg/ml) of the cytostatic drug Etoposid only partially block the apoptosis reducing effect of MDPK67b.

Example 6

RT-PCR Analysis of KLK Expression in Leukemic Cell Lines and Donor Derived Mononuclear and Neutrophil Cells Material and Methods:
DU-145, PC-3, T47D, OVCAR-3, HL-60, THP1 and U937 cell lines were cultured in appropriate standard media with 10% deactivated fetal calf serum and incubated at 37° C. with 5% CO2. Mononuclear and neutrophil cells were isolated. Total RNA was extracted from the cells using Trizol reagent (Life Technologies, Inc.) and PureLink Micro-to-Midi kit (Invitrogen) and two µg of total RNA were reverse-transcribed into first-strand cDNA using Superscript III (Invitrogen) in a 20-µl reaction following the manufacturer's instructions.

PCR reactions were performed using specific primers for each kallikrein and actin primers as control. All primers were already described in literature (Harvey T J et al., J Biol Chem, 2000 Dec 1;275(48):37397-406. Yousef G M et al., J Biol Chem. 2001 Jan 5;276(1):53-61. Yousef G M et al., Cancer Res. 2001 Apr 15;61(8):3425-31). Depending on the PCR reaction, RNA isolated from different cell lines including DU-145, PC-3, T47D, OVCAR-3 were used as positive controls for KLK expression (Harvey T J et al., J Biol Chem, 2000 Dec 1;275(48):37397-406).

The cycling conditions were depending on the target gene and mainly as described in Harvey T J et al., (J Biol Chem, 2000 Dec 1;275(48):37397-406). The PCR mixture was electrophoresed on a 2% agarose gel and visualized by ethidium bromide staining. Where indicated, DNA bands of the predicted size were excised from a second 2% agarose gel following electrophoresis and DNA recovered was sequenced.

Primers Used for RT-PCR KLK Amplification;

| KLK | PRIMER | Sequence ID Number | Sequence |
|---|---|---|---|
| KLK1 | KLK1 F | 45 | TGGAGAACCACACCCGCCAAG |
|  | KLK1R | 46 | ACGGCGACAGAAGGCTTATTG |
| KLK2 | KLK2 F | 47 | GCCTAAAGAAGAATAGCCAGGT |
|  | KLK2R | 48 | CTCAGACTAAGCTCTAGCACAC |
| KLK3 | KLK3 F | 49 | GCATCAGGAACAAAAGCGTGA |
|  | KLK3R | 50 | CCTGAGGAATCGATTCTTCAG |
| KLK4 | KLK4F | 51 | GCGGCACTGGTCATGGAAAAGG |
|  | KLK4R | 52 | CAAGGCCCTGCAAGTACCCG |
| KLK5 | KLK5 F | 53 | GAGCTGGGGCCGGGAAGAC |
|  | KLK5R | 54 | TGGGCCGGGCACAAGGGTAA |
| KLK6 | KLK6 F | 55 | GAGCGGCCATGAAGAAGC |
|  | KLK6R | 56 | AATCACCATCTGCTGTCTTGC |
| KLK7 | KLK7 F | 57 | GCCCAGGGTGACAAGATTATT |
|  | KLK7R | 58 | GTACCTCTGCACACCAACGG |
| KLK8 | KLK8 F | 59 | TACTCTGTGGCGGTGTCCTTG |
|  | KLK8R | 60 | GAGCCCAGGATGTGATGCCC |
| KLK9 | KLK9 F | 61 | GGCCGGCCTCTTCCACCTTAC |
|  | KLK9R | 62 | GCGCGGGCTCAGTTCTCCAT |
| KLK10 | KLK10 F | 63 | GCGGAAACAAGCCACTGTGGG |
|  | KLK10R | 64 | GGTAAACACCCCACGAGAGGA |
| KLK11 | KLK11 F | 65 | CCGCTACATAGTTCACCTGG |
|  | KLK11R | 66 | AGGTGTGAGGCAGGCGTAACT |
| KLK12 | KLK12 F | 67 | TGGCAGACAAAGAGACAAGGT |
|  | KLK12R | 68 | CTTAGAAGGGCTGGCAGGAG |
| KLK13 | KLK13 F | 69 | CTACACCTGCTTCCCCCACTCTCA |
|  | KLK13R | 70 | GCCGGTCAGGTTGCCCACAT |
| KLK14 | KLK14 F | 71 | CTGGGCAAGCACAACCTGAG |
|  | KLK14R | 72 | GCATCGTTTCCTCAATCCAGC |
| KLK15 | KLK15 F | 73 | CAAGTGGCTCTCTACGAGCG |
|  | KLK15R | 74 | ATCACACGGGTGGTCATGTG |

Results:

TABLE 2

Expression patterns of the 15 KLK genes obtained by RT-PCR analysis in leukemic cell lines and donor derived mononuclear and neutrophil cells.

| | HL60 | THP1 | U937 | Mononuclear | Neutrophil |
|---|---|---|---|---|---|
| KLK1 | ++ | ++[1] | | ++[1] | +[1] |
| KLK2 | + | + | +[1] | +[1] | |
| KLK3 | | | | | |
| KLK4 | | | | | |
| KLK5 | | | | + | |
| KLK6 | | | | | |
| KLK7 | | | | | |
| KLK8 | | | + | | + |
| KLK9 | | | ++ | | |
| KLK10 | | + | | | |
| KLK11 | | + | + | | |
| KLK12 | + | + | + | + | ++ |
| KLK13 | +[1] | ++ | | | |
| KLK14 | ++ | | + | ++ | |
| KLK15 | | | + | | |

The following symbols used represent:
++, moderate/high expression;
+, low expression;
[1] PCR products of the predicted size sequenced and confirmed to be the correct sequence.

Conclusion:

RT-PCR analysis of KLK expression levels in leukemic cell lines and isolated human blood cells indicated that multiple KLKs are expressed and that the different cells have very diverse expression patterns for the KLK protease family. Such differences in KLK expression levels might be involved in different effects kallikrein inhibitors have on in vitro cultures of these cells as the described protection against apoptosis in neutrophil cells.

DNA Sequence ACT variants: MD 820        SEQ ID NO 1

ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGMCCAGCA

-continued

CCTCCTGCGCACCCTCAATCAGTCCAGCGATGAGCTGCAGCTGAGTATGGGAAAT

GCCATGT'TTGTCAAAGAGCAACTCAGTCTGCTGGACAGGTTCACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGAAAATCACAGA

TCTGATCAAGGACCTTGACTCGCAGACAATGATGGTCCTGGTGAATTACATCTTC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

GGTCAAAATCACCCTCC<u>G</u>TTCT<u>CGA</u><u>GC</u>AGTGGAGAC<u>GCG</u>TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

Protein Sequence ACT variants: MD 820         SEQ ID NO 2
MRGSHHHHHHSRHPNSPLDEENLTQENQDRGTHVDLGLASANVDFAFSLYKQLVL

KAPDKNVIFSPLSISTALAFLSLGAHNTTLTEILKGLKFNLTETSEAEIHQSFQHLLRTL

NQSSDELQLSMGNAMFVKEQLSLLDRFTEDAKRLYGSEAFATDFQDSAAAKKLIND

YVKNGTRGKITDLIKDLDSQTMMVLVNYIFFKAKWEMPFDPQDTHQSRFYLSKKKW

VMVPMMSLHHLTIPYFRDEELSCTVVELKYTGNASALFILPDQDKMEEVEAMLLPET

LKRWRDSLEFREIGELYLPKFSISRDYNLNDILLQLGIEEAFTSKADLSGTTGARNLAVS

QVVHKAVLDVFEEGTEASAATAVKITL<u>RS</u>R<u>A</u>VETRTIVRFNRPFLMIIVPTDTQNIFFM

SKVTNPKQA*

DNA Sequence ACT variant: MD 62              SEQ ID NO 3
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGAC'TTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGCTTCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGAAAATCACAGA

TCTGATCAAGGACCTTGACTCGCAGACAATGATGGTCCTGGTGAATTACATCTTC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

<u>GGTCAAAATCACC<i>AGGAGG</i>TCT<i>ATCGAT</i></u>GTGGAGAC<u>GCG</u>TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

```
Protein Sequence ACT variant: MD 62                 SEQ ID NO 4
```
MRGSHHHHHHSRHPNSPLDEENLTQENQDRGTHVDLGLASANVDFAFSLYKQLVL

KAPDKNVIFSPLSISTALAFLSLGAHNTTLTEILKGLKFNLTETSEAEIHQSFQHLLRTL

NQSSDELQLSMGNAMFVKEQLSLLDRFTEDAKRLYGSEAFATDFQDSAAAKKL1ND

YVKNGTRGKITDLIKDLDSQTMMVLVNYIFFICAKWEMPFDPQDTHQSRFYLSKKKW

VMVPMMSLHHLTIPYFRDEELSCTVVELKYTGNASALFILPDQDKMEEVEAMLLPET

LKRWRDSLEFREIGELYLPKFSISRDYNLNDILLQLGIEEAFTSKADLSGTTGARNLAVS

QVVHICAVLDVFEEGTEASAATAVKIT<u><i>RRSID</i></u>VETRTIVRFNRPFLMIIVPTDTONIFFM

SKVTNPKQA*

```
DNA Sequence ACT variant: MD 83                    SEQ ID NO 5
```
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGCTTCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGGAAAATCACAGA

TCTGATCAAGGACCTTGACTCGCAGACAATGATGGTCCTGGTGAATTACATCITC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

<u>GGTCAAAATCA<i>GGGGGAGA</i>TCTG<i>AG</i></u>TTAGTGGAGAC<u>GCG</u>TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

Protein Sequence ACT variant: MD 83                SEQ ID NO 6
MRGSHHHHHHSRHPNSPLDEENLTQENQDRGTHVDLGLASANVDFAFSLYKQLVLK

APDKNVIFSPLSISTALAFLSLGAHNTTLTEILKGLKFNLTETSEAEIHQSFQHLLRTLN

QSSDELQLSMGNAMFVKEQLSLLDRFTEDAKRLYGSEAFATDFQDSAAAKKLINDY

VKNGTRGKITDLIKDLDSQTMMVLVNYIFFKAKWEMPFDPQDTHQSRFYLSKICKWV

MVPMMSLHHLTIPYFRDEELSCTVVELKYTGNASALFILPDQDKMEEVEAMLLPETL

KRWRDSLEFREIGELYLPKFSISRDYNLNDILLQLGIEEAFTSKADLSGITGARNLAVS

QVVHKAVLDVFEEGTEASAATAVKI*RGRS*ELVETRTIVRFNRPFLMIIVPTDTONIFFM

SKVTNPKQA*

DNA Sequence ACT variant: MD 67                  SEQ ID NO 7
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGMCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCMGCCACTGACTTTCAGGACTCAGCTGCAGC

TAAGAAGCTCATCAACGACTACGTGAAGAATGGAACTAGGGGGAAAATCACAGA

TCTGATCAAGGACCTTGACTCGCAGACAATGATGGTCCTGGTGAATTACATCTTC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

GGTCAAAATCA*AGCT*TAGAA*CAA*CATTAGTGGAGAC*GCG*TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

Protein Sequence ACT variant: MD 67                SEQ ID NO 8
MRGSHHHHHHSRHPNSPLDEENLTQENQDRGTHVDLGLASANVDFAFSLYKQLVLK

APDKNVIFSPLSISTALAFLSLGAHNTTLTEILKGLKFNLTETSEAEIHQSFQHLLRTLN

QSSDELQLSMGNAMFVKEQLSLLDRFTEDAKRLYGSEAFATDFQDSAAAKKLINDY

VKNGTRGKITDLIKDLDSQTMMVLVNYIFFKAKWEMPFDPQDTHQSRFYLSKKKWV

MVPMMSLHHLTIPYFRDEELSCTVVELKYTGNASALFILPDQDKMEEVEAMLLPETL

KRWRDSLEFREIGELYLPKFSISRDYNLNDILLQLGTEEAFTSKADLSGITGARNLAVS

QVVHKAVLDVFEEGTEASAATAVKI*KLRTT*LVETRTIVRFNRPFLMIIVPTDTQNIFFM

SKVTNPKQA*

DNA Sequence ACT variant: MD 61              SEQ ID NO 9
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTICAACCTCACGGAGACTICTGAGGCAGAAATTCACCAGAGCTICCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGGAAAATCACAGA

TCTGATCAAGGACCTTGACTCGCAGACAATGATGGTCCTGGTGAATTACATCTTC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTITCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

G*GTCAAAATCATGACAAGA*TCT*AACGC*AGTGGAGAC*GCG*TACCATTGTGCGTTTC

KACAGGCCCTTCCTGATGATCATIGTCCCTACAGACACCAGAACATCTTCTTCAT

GAGCAAAGTCACCAATCCCAAGCAAGCCTAA

Protein Sequence ACT variant: MD 61             SEQ ID NO 10
MRGSHHHHHHSRHPNSPLDEENLTQENQDRGTHVDLGLASANVDFAFSLYKQLVLK

APDKNVIFSPLSISTALAFLSLGAHNTTLTEILKGLKFNLTETSEAEIHQSFQHLLRTLN

QSSDELQLSMGNAMFVKEQLSLLDRFTEDAKRLYGSEAFATDFQDSAAAKKLINDY

VKNGTRGKITDLIKDLDSQTMMVLVNYIFFKAKWEMPFDPQDTHQSRFYLSKKKWV

MVPMMSLHHLTIPYFRDEELSCTVVELKYTGNASALFILPDQDKMEEVEAMLLPETL

KRWRDSLEFREIGELYLPKFSISRDYNLNDILLQLGIEEAFTSKADLSGITGARNLAVS

QVVHKAVLDVFEEGTEASAATAVKI*MTRSNA*VETRTIVRFNRPFLMIIVPTDTIONIFF

MSKVTNPKQA*

DNA Sequence ACT variants: MD 518           SEQ ID NO 11
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACFTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGITCAACCTCACGGAGACTTCTGAGGCAGAAATTCACCAGAGCTTCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTICACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGAAAATCACAGA

TCTGATCAAGGACCTTGACTCGCAGACAATGATGGTCCTGGTGAATTACATCTTC

TTTAAAGCCAAATGGGAGATGCCCMGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

GGTCAAAATCACC*GAGCGTGTGTCGCCC*GTGGAGAC*GCG*TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

Protein Sequence ACT variants: MD 518                    SEQ ID NO 12
MRGSHHHHHHSRHPNSPLDEENLTQENQDRGTHVDLGLASANVDFAFSLYKQLVL

KAPDKNVIFSPLSISTALAFLSLGAHNTTLTEILKGLKFNLTETSEAEIHQSFQHLLRTL

NQSSDELQLSMGNAMFVKEQLSLLDRFTEDAKRLYGSEAFATDFQDSAAAKKLIND

YVKNGTRGKITDLIKDLDSQTMMVLVNYIFFKAKWEMPFDPQDTHQSRFYLSKKKW

VMVPMMSLHHLTIPYFRDEELSCTVVELKYTGNASALFILPDQDKMEEVEAMLLPET

LKRWRDSLEFREIGELYLPKFSISRDYNLNDILLQLGIEEAFTSKADLSGITGARNLAVS

QVVHKAVLDVFEEGTEASAATAVKIT*ERVSP*VETRTIVRFNRPFLMIIVPTDTQNIFFM

SKVTNPKQA*

DNA Sequence ACT variants: MDCI                         SEQ ID NO 13
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGCTTCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCMGCCACTGACTTTCAGGACTCAGCTGCAGC

TAAGAAGCTCATCAACGACTACGTGAAGAATGGAACTAGGGGGAAAATCACAGA

TCTGATCAAGGACCTTGACTCGCAGACAATGATGGTCCTGGTGAATTACATCTTC

```
TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTITCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

GGTCAAAATCACC_TT__TAGA_TCTGCATTAGTGGAGAC_GCG_TACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA
```

Protein Sequence ACT variants: MD CI                SEQ ID NO 14
MRGSHHHHHHSRHPNSPLDEENLTQENQDRGTHVDLGLASANVDFAFSLYKQLVL

KAPDKNVIFSPLSISTALAFLSLGAHNTTLTEILKGLKFNLTETSEAEIHQSFQHLLRTL

NQSSDELQLSMGNAMFVKEQLSLLDRFTEDAKRLYGSEAFATDFQDSAAAKKLIND

YVKNGTRGKITDLIKDLDSQTMMVLVNYIFFKAKWEMPFDPQDTHQSRFYLSKKKW

VMVPMMSLHHLTIPYFRDEELSCTVVELKYTGNASALFTLPDQDKMEEVEAMLLPET

LKRWRDSLEFREIGELYLPKFSISRDYNLNDILLQLGIEEAFTSKADLSGITGARNLAVS

QVVHKAVLDVFEEGTEASAATAVKIT_FR_SALVETRTIVRFNRPFLMIIVPTDTQNIFFM

SKVTNPKQA*

```
DNA sequence of MDPK67b                            SEQ ID NO 15
ATGCATCCGAACAGCCCGCTGGATGAAGAAAACCTGACCCAGGAAAACCAGGAT

CGCGGCACCCATGTGGATCTGGGTCTGGCCAGCGCGAACGTGGATTTTGCGTTCA

GCCTGTATAAACAGCTGGTGCTGAAAGCGCCGGATAAAAACGTGATTTTTAGCCC

GCTGTCTATTAGCACCGCGCTGGCCTTTCTGAGCCTGGGCGCGCATAACACCACC

CTGACCGAAATTCTGAAAGGCCTGAAATTTAACCTGACCGAAACCAGCGAAGCG

GAAATTCATCAGAGCTTTCAGCATCTGCTGCGTACCCTGAACCAGAGCAGCGATG

AACTGCAGCTGTCTATGGGCAACGCGATGTTTGTGAAAGAACAGCTGTCTCTGCT

GGATCGTTTTACCGAAGATGCGAAACGTCTGTATGGCAGCGAAGCGTTTGCGACC

GATTITCAGGATAGCGCGGCGGCGAAAAAACTGATTAACGATTATGTGAAAAAC

GGCACCCGTGGCAAAATTACCGATCTGATCAAAGATCTGGATAGCCAGACCATG

ATGGTGCTGGTGAACTACATCTTCTTCAAAGCGAAATGGGAAATGCCGTTTGATC

CGCAGGATACCCATCAGAGCCGTTTTTACCTGAGCAAAAAAAAATGGGTGATGGT

GCCGATGATGAGCCTGCATCATCTGACCATTCCGTATTTTCGTGATGAAGAACTG

AGCTGCACCGTGGTGGAACTGAAATATACCGGCAACGCGAGCGCGCTGTTTATTC

TGCCGGATCAGGATAAAATGGAAGAAGTGGAAGCGATGCTGCTGCCGGAAACCC

TGAAACGTTGGCGTGATAGCCTGGAATTTCGTGAAATTGGCGAACTGTATCTGCC

GAAATTTAGCATTAGCCGCGATTATAACCTGAACGATATTCTGCTGCAGCTGGGC

ATTGAAGAAGCGTTTACCAGCAAAGCGGATCTGAGCGGCATTACCGGTGCGCGT

AACCTGGCCGTGAGCCAGGTGGTGCATAAAGCGGTGCTGGATGTGTTTGAAGAA
```

```
GGCACCGAAGCGAGCGCGGCGACCGCGGTGAAAATTAAACTGCGTACCACCCTG

GTGGAAACCCGTACCATTGTGCGTTTTAACCGTCCGTTTCTGATGATTATTGTGCC

GACCGATACCCAGAACATCTTTTTCATGAGCAAAGTGACCAATCCGAAACAGGCG

TAA

Amino acid sequence of MDPK67b                           SEQ ID NO 16
MHPNSPLDEENLTQENQDRGTHVDLGLASANVDFAFSLYKQLVLKAPDKNVIFSPLSI

STALAFLSLGAHNTTLTEILKGLKFNLTETSEAEIHQSFQHLLRTLNQSSDELQLSMGN

AMFVKEQLSLLDRFTEDAKRLYGSEAFATDFQDSAAAKKLINDYVKNGTRGKTTDLI

KDLDSQTMMVLVNYIFFKAKWEMPFDPQDTHQSRFYLSKKKWVMVPMMSLHHLTI

PYFRDEELSCTVVELKYTGNASALFILPDQDKMEEVEAMLLPETLKRWRDSLEFREIG

ELYLPKISISRDYNLNDILLQLGIEEAFTSKADLSGITGARNLAVSQVVHKAVLDVFEE

GTEASAATAVKIKLRTTLVETRTIVRFNRPFLMIIVPTDTQNIFFMSKVTNPKQA

DNA sequence of ACT-G9
(alternative names: MDOKG9, OKDG9)                        SEQ ID NO 17
ATGAGAGGATCCCATCACCATCACCATCACTCTAGACACCCTAACAGCCCACTT

GACGAGGAGAATCTGACCCAGGAGAACCAAGACCGAGGGACACACGTGGACCTC

GGATTAGCCTCCGCCAACGTGGACTTCGCTTTCAGCCTGTACAAGCAGTTAGTCC

TGAAGGCCCCTGATAAGAATGTCATCTTCTCCCCACTGAGCATCTCCACCGCCTTG

GCCTTCCTGTCTCTGGGGGCCCATAATACCACCCTGACAGAGATTCTCAAAGGCC

TCAAGTTCAACCTCACGGAGACTTCTGAGGCAGAAATTCACCAGAGCTTCCAGCA

CCTCCTGCGCACCCTCAATCAGTCCAGCGATGAGCTGCAGCTGAGTATGGGAAAT

GCCATGTTTGTCAAAGAGCAACTCAGTCTGCTGGACAGGTTCACGGAGGATGCCA

AGAGGCTGTATGGCTCCGAGGCCTTTGCCACTGACTTTCAGGACTCAGCTGCAGC

TAAGAAGCTCATCAACGACTACGTGAAGAATGGAACTAGGGGGAAAATCACAGA

TCTGATCAAGGACCTTGACTCGCAGACAATGATGGTCCTGGTGAATTACATCTTC

TTTAAAGCCAAATGGGAGATGCCCTTTGACCCCCAAGATACTCATCAGTCAAGGT

TCTACTTGAGCAAGAAAAAGTGGGTAATGGTGCCCATGATGAGTTTGCATCACCT

GACTATACCTTACTTCCGGGACGAGGAGCTGTCCTGCACCGTGGTGGAGCTGAAG

TACACAGGCAATGCCAGCGCACTCTTCATCCTCCCTGATCAAGACAAGATGGAGG

AAGTGGAAGCCATGCTGCTCCCAGAGACCCTGAAGCGGTGGAGAGACTCTCTGG

AGTTCAGAGAGATAGGTGAGCTCTACCTGCCAAAGTTTTCCATCTCGAGGGACTA

TAACCTGAACGACATACTTCTCCAGCTGGGCATTGAGGAAGCCTTCACCAGCAAG

GCTGACCTGTCAGGGATCACAGGGGCCAGGAACCTAGCAGTCTCCCAGGTGGTCC

ATAAGGCTGTGCTTGATGTATTTGAGGAGGGCACAGAAGCATCTGCTGCCACCGC

GGTCAAAACCGTTGACTACGCTGCTCTGGTGGAGACGCGTACCATTGTGCGTTTC

AACAGGCCCTTCCTGATGATCATTGTCCCTACAGACACCCAGAACATCTTCTTCAT

GAGCAAAGTCACCAATCCCAAGCAAGCCTAA

Amino acid sequence of: ACT-G9
(alternative names: MDOKG9, OKDG9)                        SEQ ID NO 18
MRGSHHHHHHSRHPNSPLDEENLTQENQDRGTHVDLGLASANVDFAFSLYKQLVL

KAPDKNVIFSPLSISTALAFLSLGAHNTTLTEILKGLKFNLTETSEAEIHQSFQHLLRTL

NQSSDELQLSMGNAMFVKEQLSLLDRFTEDAKRLYGSEAFATDFQDSAAAKKLIND
```

YVKNGTRGKITDLIKDLDSQTMMVLVNYIFFKAKWEMPFDPQDTHQSRFYLSKICKW

VMVPMMSLHHLTIPYFRDEELSCTVVELKYTGNASALFILPDQDKMEEVEAMLLPET

LKRWRDSLEFREIGELYLPKFSISRDYNLNDILLQLGIEEAFTSKADLSGITGARNLAVS

QVVHKAVLDVFEEGTEASAATAVK*TVDYA*ALVETRTIVRFNRPFLMIIVPTDTQNIFF

MSKVTNPKQA*

*Italic*: start codon ATG
Bold: His-tag
Underlined: DNA mutation
*Underlinedanditalic*: DNA sequence encoding RSL mutation.

The invention claimed is:

1. A method of inhibiting neutrophil apoptosis in a patient having or suspected of having neutropenia, the method comprising:
   administering to the patient a therapeutically effective amount of at least one Kallikrein inhibitor including the full-length amino acid sequence of SEQ ID NO:16 or SEQ ID NO:18.

2. The method of claim 1, wherein the administered amount is an amount effective to treat irradiation induced damage of myeloid cells in said patient.

3. The method of claim 1, wherein the Kallikrein inhibitor is directed against an hK2 or hK14 protease.

4. The method of claim 1, wherein prior to the administration of the Kallikrein inhibitor, the number and/or activation state of neutrophils in the patient is impaired.

5. The method of claim 1, wherein the Kallikrein inhibitor includes the full-length amino acid sequence of SEQ ID NO:16.

6. The method of claim 1, wherein the Kallikrein inhibitor includes the full-length amino acid sequence of SEQ ID NO:18.

7. A method of inhibiting neutropenia in a patient, comprising:
   administering to the patient a therapeutically effective amount of at least one Kallikrein inhibitor including the full-length amino acid sequence of SEQ ID NO:16 or SEQ ID NO:18.

8. The method of claim 7, wherein the Kallikrein inhibitor includes the full-length amino acid sequence of SEQ ID NO:16.

9. The method of claim 7, wherein the Kallikrein inhibitor includes the full-length amino acid sequence of SEQ ID NO:18.

10. A method comprising:
    administering to a patient a therapeutically effective amount of at least one Kallikrein inhibitor including the full-length amino acid sequence of SEQ ID NO:16 or SEQ ID NO:18:
    (1) during and after transfection of bone marrow cells,
    (2) during blood stem cell mobilization performed for reconstitution of hematopoiesis, and/or
    (3) during infusion of cells of the myeloid lineage for reconstitution of hematopoiesis or for treatment of neutropenia by infusion of neutrophils.

11. The method of claim 10, wherein the Kallikrein inhibitor includes the full-length amino acid sequence of SEQ ID NO:16.

12. The method of claim 10, wherein the Kallikrein inhibitor includes the full-length amino acid sequence of SEQ ID NO:18.

* * * * *